US009492368B2

(12) United States Patent
Ishihara et al.

(10) Patent No.: US 9,492,368 B2
(45) Date of Patent: Nov. 15, 2016

(54) EXTERNAL PREPARATION FOR SKIN

(75) Inventors: Tatsuya Ishihara, Okayama (JP); Shimpei Ushio, Okayama (JP); Rohko Yamamoto, Okayama (JP); Takanori Ohkura, Okayama (JP); Shigeharu Fukuda, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 511 days.

(21) Appl. No.: 13/983,231

(22) PCT Filed: Jan. 31, 2012

(86) PCT No.: PCT/JP2012/052118
§ 371 (c)(1),
(2), (4) Date: Aug. 1, 2013

(87) PCT Pub. No.: WO2012/105542
PCT Pub. Date: Aug. 9, 2012

(65) Prior Publication Data
US 2013/0309188 A1    Nov. 21, 2013

(30) Foreign Application Priority Data
Feb. 1, 2011    (JP) ................ 2011-020233

(51) Int. Cl.
| *A61K 8/60* | (2006.01) |
| *C07H 19/167* | (2006.01) |
| *A61Q 19/08* | (2006.01) |
| *A61Q 19/00* | (2006.01) |
| *A61Q 19/02* | (2006.01) |
| *A61K 9/00* | (2006.01) |
| *C12P 19/18* | (2006.01) |
| *C12P 19/40* | (2006.01) |

(52) U.S. Cl.
CPC .............. *A61K 8/602* (2013.01); *A61K 8/606* (2013.01); *A61K 9/0014* (2013.01); *A61Q 19/00* (2013.01); *A61Q 19/001* (2013.01); *A61Q 19/02* (2013.01); *A61Q 19/08* (2013.01); *C07H 19/167* (2013.01); *C12P 19/18* (2013.01); *C12P 19/40* (2013.01); *C12Y 204/01019* (2013.01); *Y02P 20/52* (2015.11)

(58) Field of Classification Search
CPC .... A61K 8/606; A61K 8/4953; A61K 8/602; A61K 9/0014; C07H 19/16; C07H 19/20; C12P 19/40; C12P 19/18; C12Y 204/01019
See application file for complete search history.

(56) References Cited

U.S. PATENT DOCUMENTS

2013/0129651 A1    5/2013   Miyake et al.

FOREIGN PATENT DOCUMENTS

| EP | 1424064 A1 | 6/2004 |
| EP | 2204154 A1 | 7/2010 |
| EP | 2601930 A1 | 6/2013 |
| JP | 50-63189 A | 5/1975 |
| JP | 8-127590 A | 5/1996 |
| JP | 8-507289 A | 8/1996 |
| JP | 8-337593 A | 12/1996 |
| JP | 8-124499 A | 5/1997 |
| JP | 2001510777 A | 8/2001 |
| JP | 3495217 B2 | 2/2004 |
| JP | 2007186471 A | 7/2007 |
| JP | 2009-149557 A | 7/2009 |
| JP | 2010-155834 A | 7/2010 |
| WO | 01/90338 A1 | 11/2001 |
| WO | 02/10361 A1 | 2/2002 |
| WO | 2005/034902 A1 | 4/2005 |
| WO | 2005/044205 A1 | 5/2005 |
| WO | 2008/136331 A1 | 11/2008 |

OTHER PUBLICATIONS

Ozbun et al., Plant Physiol., 1971, 48, 765-769.*
Suzuki et al., Yukio, Science & Industry, vol. 65, No. 6, pp. 265-274, (1991).
Takahashi et al., Shuji, "Adenophostins A and B: Potent Agonists of Inositol-1,4,5- Trisphosphate Receptor Produced by Penicillium Brevicompactum Structure Elucidation", The Journal of Antibiotics, vol. 47, No. 1, pp. 95-100, (1994).
Suzuki et al., Yukio, "Biosytheses of Adenosine 5'-α-glucoside by Aspergillus Niger", Vitamins, vol. 44, No. 4, pp. 196-200, (1971).
European search report dated Jul. 20, 2015, in corresponding application No. EP12741490.2.

* cited by examiner

*Primary Examiner* — Kyle Purdy
(74) *Attorney, Agent, or Firm* — Browdy and Neimark, PLLC

(57) ABSTRACT

The present invention has an object to provide an external dermal agent with a sustainable anti-wrinkle action, which has both the action of enhancing the proliferation and differentiation of keratinocytes in the skin and the action of enhancing the collagen production in the skin, and which assists the maintenance and the improvement of tissue structures and physiological functions of the epidermis and the dermis, whereby providing a remarkable skin improvement effect. The present invention solves the above object by providing an external dermal agent containing α-D-glucopyranosyl-(1→3')-adenosine and/or α-D-glucopyranosyl-(1→5')-adenosine as an effective ingredient(s).

3 Claims, No Drawings

EXTERNAL PREPARATION FOR SKIN

TECHNICAL FIELD

The present invention relates to a sustainable external dermal agent for anti-wrinkles, which contains α-D-glucopyranosyl-(1→3')-adenosine and/or α-D-glucopyranosyl-(1→5')-adenosine (called, respectively, "3'-glucosyladenosine" and "5'-glucosyladenosine", hereinafter, and they may be collectively called "glucosyladenosines") as an effective ingredient(s).

BACKGROUND ART

The skin is constructed by the outer thin epidermis (epithelium tissue) that forms the outermost layer of the body, protects living bodies from the outside world, and plays a role of preventing the body moisture and nutrients from escaping from the body; and the thick dermis (connective tissue) that has a complexly, three-dimensionally extending structure of fibroblasts, collagen fibers, elastic fibers, proteoglycans, etc., mainly. Skin conditions are maintained by the epidermis and the dermis while keeping their respective normal tissue structures and physiological functions.

The epidermis of the skin is classified into "stratum basale", "stratum spinosum", "stratum granulosum", and "stratum corneum", from the side of the dermis, and is mainly composed of cells called keratinocytes. Such keratinocytes form a monolayer as immature cells with proliferating ability in the undermost layer stratum basale, differentiate (keratinization) while proliferating and growing and being boosted toward the upper layer, and finally turn into corneocytes as death cells with no nuclei for forming stratum corneum, which are then sequentially desquamated from the surface layer part of the stratum corneum. Cutaneous homeostasis is maintained by a constantly-cyclic-smooth-turnover of a process of proliferation, passage, differentiation, and desquamation of keratinocytes in the epidermis of the skin.

The skin, however, is deteriorated to lose its moisture by different factors such as ageing, drying, oxidation, and sunlight (ultraviolet rays), resulting in showing various phenomena such as the generation of wrinkles and sagging skin and the reduction of skin firmness and elasticity. One of the main causatives of such skin deterioration has been recognized as the reduction of collagen synthesis by fibroblasts to lower the collagen level in the dermis; there have been explored various external dermal agents and food products, in which incorporated collagen or agents for augmenting collagen production to improve the reduction of collagen level (see, for example, Japanese Patent No. 3495217 and Japanese Patent Kokai No. 2007-186471).

In the epidermis that constitutes the outermost layer of the body, undesirable conditions that would be factors for inducing wrinkles may be induced: As the inhibition of the proliferation and the differentiation of keratinocytes that constitute the epidermis, supplying of corneocytes from the lower layer and forming of keratinous layer in the upper layer are reduced; the thickening and the moisture reduction or the like in the keratinous layer are induced by the interruption of turnover of keratinous layer; and the moisturizing- and barrier-functions of keratinous layer are lowered. When the drying in the skin proceeds due to a relatively low-humid environment, excessive skin-washing, ageing, constitution, etc., multiple peeling of keratinous layer becomes to be easily induced and to cause drawbacks such as the reduction of skin gloss and the deterioration of smooth makeup, as well as inducing skin troubles such as the generation of wrinkles, rough skin, etc. To improve such skin troubles, trials for enhancing the proliferation and the differentiation of keratinocytes have been made, and compositions for use in the skin, into which substances capable of enhancing the differentiation of keratinocytes are incorporated, have been proposed (see, for example, Japanese Patent Application Prior-to-Examination Publication (Tokuhyo) Nos. 2001-510777 and 507289/96).

As described above, various substances, which improve the deterioration of skin conditions including the generation of wrinkles, i.e., which improves the reduction of collagen-producing ability in the dermis and the deterioration of the turnover of keratinous layer in the epidermis, and compositions used for the skin have been variously proposed. Since all the above concern only on the improvement of the symptom of the epidermis or the dermis, their anti-wrinkle actions are not successfully satisfactory. Accordingly, there has been desired a development of an external dermal agent that improves the symptoms in both the epidermis and the dermis, keeps comprehensively cutaneous homeostasis, and imparts a high anti-wrinkle action. Japanese Patent Kokai No. 2009-149557 discloses prolactin, as an example of substances having the above functions, which has drawbacks, due to its nature of a peptide, in stability, permeability into the stratum basale, etc., when formulated into preparations or applied to the skin as an external agent. To overcome these drawbacks, there have been eagerly anticipated a novel ingredient that has a satisfactory anti-wrinkle action through its action on both the epidermis and the dermis and also has an improved sustainable effect, and an external dermal agent with such an ingredient.

DISCLOSURE OF INVENTION

In view of the above, the present invention has an object to provide a novel sustainable external dermal agent for anti-wrinkles, which sustainably assists the improvement of tissue structures and physiological functions of both the epidermis and the dermis, brings a skin-improving effect, has an action of maintaining the skin in normal conditions, has a satisfactory stableness even when applied to the skin, and has a satisfactory safeness without affecting living bodies.

The present inventors focused on nucleic acid-related substances to solve the above object, and, during their energetic continuous studying and repeated trials and errors, they selected and studied adenosine that intrinsically exists in living bodies in view of its safeness against living bodies. Adenosine per se has been known to have an action of augmenting the collagen production in the dermis and the proliferation of keratinocytes by dermal papilla cells (see, for example, International Patent Publication Nos. WO05/034902 and WO05/044205), and revealed by the researches of the present inventors that adenosine may be difficult to sustain its effect because it is promptly metabolized by an enzyme existing intrinsically in living bodies, and the handling accompanies difficulty when incorporated in external dermal agents due to its relatively low solubility in hydrophilic media. To solve the above problem, the present inventors further continued studying and found that 3'-glucosyladenosine and/or 5'-glucosyladenosine, where a D-glucose residue binds via α-linkage to the hydroxy group at the C-3' or C-5' position of adenosine (the C-3 or C-5 position of the ribose of adenosine molecule), act on keratinocytes in the epidermis and have significantly superior actions of enhancing the proliferation and the differentiation of keratinocytes to adenosine.

The present inventors found that the above glucosyladenosines also act on fibroblasts of the dermis and have a significantly superior action of enhancing the collagen production to adenosine.

Further, the present inventors found that, unlike glycosides such as ascorbic acid 2-glucoside, the above glucosyladenosines are unexpectedly unsusceptible to the action of degrading enzymes present in living bodies, and they are more stable and superior to adenosine in their effect sustainability in living bodies' environments.

The present inventors further found that the above glucosyladenosines have superior solubility in hydrophilic media to adenosine.

The present inventors found that the above glucosyladenosines are safe substances even when applied to humans because they are hardly induce cytotoxicity compared to adenosine and gradually decomposed even though they are more stable than adenosine in living bodies as disclosed in the above, and the formed adenosine is promptly metabolized; and they confirmed that the glucosyladenosines are more useful than adenosine in terms of the strength of effects, sustainability, and safeness as effective ingredients for external dermal agents with an anti-wrinkle action. Thus, they accomplished the present invention.

The present invention solves the above object by providing a sustainable external dermal agent with an anti-wrinkle action, which contains 3'-glucosyladenosine and/or 5'-glucosyladenosine as an effective ingredient(s).

Although 3'-glucosyladenosine and 5'-glucosyladenosine per se are known substances as disclosed in "*Science & Industry*", Yukio Suzuki and Kei Uchida, Vol. 65, No. 6, pp. 265-274, 1991, and "*The Journal of Antibiotics*", Shuji Takahashi et al., Vol. 47, No. 1, pp. 95-100, 1994, the following have never been known that the glucosyladenosines have an effect of enhancing the proliferation and the differentiation of keratinocytes in the epidermis, have an effect of enhancing the collagen production by fibroblasts in the dermis, and have an anti-wrinkle action, wherein the effects are more enhanced than by unglycosylated adenosine, and they are more stable and less unsusceptible to decomposition by enzymes present intrinsically in living bodies than adenosine, and the above effects are highly sustainable.

The external dermal agent of the present invention, which contains glucosyladenosine(s) as an effective ingredient(s), has both the action of enhancing the proliferation and the differentiation of keratinocytes in the epidermis and the action of augmenting the collagen production by fibroblasts in the dermis, it accelerates the turnover of keratinous layer in the epidermis, which has been lowered by various factors; improves the thickening of keratinous layer, the moisture reduction, etc.; improves the moisture retaining- and barrier-functions of the epidermis; and increases the collagen level in the dermis to elevate the skin firmness and elasticity. Because of these, the agent exerts an improved anti-wrinkle action, more effectively improves various skin symptoms such as rough skin, dullness, reduction of firmness and elasticity, and xerodermia; and maintains the skin in its normal conditions.

The glucosyladenosines of the present invention have superior solubilities in hydrophilic media to adenosine, and they are more easily handleable than adenosine when incorporated into external dermal agents.

Although the glucosyladenosines of the present invention are more stable than adenosine and more unsusceptible to hydrolysis with enzymes than other glycosides such as ascorbic acid 2-glucoside, they are gradually hydrolyzed into D-glucose and adenosine by the action of hydrolyzing enzymes present in living bodies, and the formed adenosine is promptly metabolized. Therefore, the glucosyladenosines are safe substances even when administered to humans and are superior in their effect sustainability to adenosine.

Since the glucosyladenosines of the present invention have an anti-wrinkle action with an improved effect sustainability, they are preferably used in external dermal agents for skin for a relatively long period of time. Desired examples of antiseptics, having an antiseptic or bacteriostatic action used for such external dermal agents, include those which have a lesser stimulation to the skin even when used successively and do not deteriorate the effects of the glucosyladenosines of the present invention, and the combination use thereof would greatly exert the effects of the present invention.

The glucosyladenosines of the present invention are stable against enzymes, etc., and unsusceptible to other ingredients, which are used in external dermal agents, when used in combination therewith; in particular, when used with natural ingredients such as plant extracts, the glucosyladenosines have a lesser fear of being decomposed by enzymes, etc., contained in the natural ingredients, and they can be made into improved external dermal agents that stably exert their anti-wrinkle actions along with the activities of the other ingredients.

Means to Attain the Object

As described above, the present invention relates to an external dermal agent with a sustainable anti-wrinkle action, which contains 3'-glucosyladenosine and/or 5'-glucosyladenosine as an effective ingredient(s).

Since the external dermal agent as referred to in the present invention contains the above glucosyladenosine(s), it has both the action of enhancing the proliferation and the differentiation of keratinocytes in the epidermis and the action of augmenting the collagen production, as well as having an improved sustainability in their effects; accordingly, it can be used to inhibit the skin deterioration including the generation of wrinkles and to improve various skin symptoms such as rough skin, dullness, reduction of skin firmness and elasticity, and xerodermia.

The glucosyladenosines used as effective ingredients of the present invention mean any of those which contain either or both of 3'-glucosyladenosine and 5'-glucosyladenosine. As described later, 5'-glucosyladenosine is superior in stability against biogenic substances such as enzymes present in living bodies and high in solubility in hydrophilic media such as water, while 3'-glucosyladenosine is feasible to exert its effects at a relatively low concentration. Accordingly, the glucosyladenosines can be preferably used in an appropriate combination depending on the formulations and the purposes of external dermal agents. The external dermal agent of the present invention may contain α-glycosyladenosine, where at least one molecule of D-glucose binds to the glucose of any of the above glucosyladenosines in an α-1,4, α-1,6 and/or α-1,3 fashions.

The glucosyladenosines used in the external dermal agent of the present invention can be prepared by enzymatic methods. They can be also prepared by fermentation methods or synthetic methods, if necessary. Enzymatic methods with glycosyltransferases would be advantageous when considering economy.

The glucosyladenosines used in the present invention should not necessarily be highly purified and the purity should not specifically be restricted as long as they have no safety problem such that they contain harmful impurities that may affect the skin and do not deteriorate the desired effects. Depending on the administration forms or formulations of the external dermal agent of the present invention, any of the following can be used; intact reaction solutions containing adenosine, as production materials, after enzymatic reactions, those in a composition form unseparated from other substances inherent to their production methods, or partially or highly purified ones. Highly purified 3'- and 5'-glucosyladenosines can be appropriately mixed prior to use depending on purposes.

The term of the action of enhancing the proliferation and the differentiation of keratinocytes in the epidermis as referred to in the present invention means any of the following steps of mitotic proliferation of keratinocytes present in the stratum basale in the epidermis, the differentiation of these cells into cells for forming stratum spinosum, stratum granulosum, and stratum corneum while such cells are boosted toward the upper layer, and finally turn into corneocytes as death cells with no nuclei; or an action of accelerating all the above steps of maintaining the epidermis in its healthy conditions. The action of augmenting the collagen production as referred to in the present invention means an action of increasing the collagen production by fibroblasts present in the dermis.

The dose of the external dermal agent of the present invention should not specifically be restricted as long as the desired effect of the present invention is attained, and the agent is administered with a daily dose at once or several times a day. A daily dose of the agent is usually 0.001 to 100 mg/cm$^2$ skin, preferably, 0.05 to 10 mg/cm$^2$ skin, and more preferably, 0.01 to 1 mg/cm$^2$ skin in terms of glucosyladenosine(s) as an effective ingredient(s). In some cases, percutaneous administration doses of less than 0.001 mg/cm$^2$ skin may not attain a desired effect and percutaneous administration doses of even over 100 mg/cm$^2$ skin may not attain effects well-balanced with such doses.

Although the glucosyladenosines of the present invention can be solely used as effective ingredients of external dermal agents, they can be arbitrarily used in the form of a composition with other medicaments having a skin-improving action, enhancing the collagen production, and enhancing the proliferation and the differentiation of keratinocytes; and further arbitrarily made into external dermal agents in the form of an appropriate composition with optional medically effective ingredients such as skin-whitening agents, antioxidants, anti-inflammatories, and humectants, thereby obtained are external dermal agents that exert both the actions of the above other medicaments and ingredients and the above-identified effects of glucosyladenosines. To the glucosyladenosines can be added appropriate carriers, fillers/excipients/adjuvants, stabilizers, buffers, pH-regulators, media, and arbitrary supplements, which can be usually used in cosmetics, pharmaceuticals, quasi-drugs, etc., and the resulting mixtures can be used in an appropriate form of a powder, granule, liquid, or the like, depending on the forms or the formulations of final products as long as the effects of the present invention are not hindered.

The composition amount of the glucosyladenosines in the external dermal agent of the present invention should not be restricted independently of its form or formulation as long as the desired effects can be attained, and usually the glucosyladenosines are incorporated in an amount of 0.001 to 30% by mass in the agent, preferably, 0.01 to 10% by mass, and more preferably, 0.1 to 5% by mass. Even when incorporated into the external dermal agent in an amount of over 30% by mass, the glucosyladenosines of the present invention may not attain a well-balanced effect with such an amount and, when incorporated in an amount of less than 0.001% by mass, the desired effects may not be attained.

The external dermal agent of the present invention enhances the proliferation and the differentiation of keratinocyte present in the epidermis, increases the supply of corneocytes, and accelerates the turnover of keratinous layer, whereby the skin conditions with reduced functions are improved and maintained in an appropriate state.

Further, the external dermal agent of the present invention enhances the expression of genes that relate to the ceramide synthesis by keratinocytes in the epidermis and to the collagen synthesis by fibroblasts in the dermis and increases the ceramide level in the epidermis and the collagen level in the dermis, whereby the skin elasticity, firmness, barrier function, etc., are enhanced and the skin conditions with reduced functions are improved to maintain the skin in an appropriate state.

Accordingly, the external dermal agent of the present invention improves the moisturizing function of the skin and prevents or improves arbitrary skin conditions such as rough skin, wrinkles, reduction of skin firmness and elasticity, reduction of skin barrier function, skin dryness, xerodermia, and psoriasis. Since glucosyladenosines have actions of enhancing the proliferation and the differentiation keratinocytes, augmenting the collagen production, and enhancing the ceramide synthesis, as well as having a moisturizing action, the external dermal agent of the present invention can be advantageously used in producing agents for enhancing the proliferation and the differentiation of keratinocytes, augmenting the collagen production, and for enhancing the ceramide synthesis, as well as in producing humectants. The external dermal agent can be used in producing expression enhancers of genes for β-glucocerebrosidase (GCase) and sphingomyelinase (SMase), which relate to ceramide synthesis.

Since the external dermal agent of the invention has an anti-wrinkle action with an improved effect sustainability and can be applied to the skin for a relatively long period of time, antimicrobials with an antiseptic or bacteriostatic action are desirably incorporated. Examples of such antiseptics include benzoic acid and salts thereof, salicylic acid and salts thereof, sorbic acid and salts thereof, dehydroacetic acid and salts thereof, p-hydroxybenzoate esters including p-hydroxybenzoic acid alkyl ester, edetic acid, 2,4,4'-trchloro-2'-hydroxydiphenylether, 3,4,4'-trichlorocarbanilide, hexachlorophene, benzalkonium chloride, phenoxyethanol, hinokitiol, resorcin, ethanol, 1,3-butylene glycol, photosensitizing dye 201, lactic acid, 1,2-alkane diols, and other plant extracts with antibacterial actions such as *Gardenia jasminoides* extract, *Sophora flavescens* extract, *Salvia officinalis* extract, *Thymus* extract, *Artemisia indica* var. *maximowiczii* extract, and *Phellodendron amurense* extract.

In particular, the external dermal agent of the present invention has a lesser stimulation to the skin even when used successively and exerts the effect of the invention highly by incorporating antiseptics that do not hinder the effects of glucosyladenosines of the present invention. Among the above antiseptics, the ingredients of non p-hydroxybenzoate esters such as 1,2-alkane diols and 1,3-butylene glycol are preferable because of their low stimuli to the skin, high antiseptic effect, and humectancy. Preferable 1,2-alkane diols are those with carbon atom numbers of 4 to 10, particularly, one or more 1,2-alkane diols selected from 1,2-pentane diol, 1,2-hexane diol, 1,2-heptane diol, and 1,2-octane diol are specifically preferable. Appropriate surfactants can be arbitrarily used for mixing to homogeneity these antiseptics and the glucosyladenosines of the present invention as long as such surfactants do not hinder the effects of the present invention.

The external dermal agent of the present invention can be used, if necessary, in the form of a composition prepared by mixing glucosyladenosines with one or more other appropriate ingredients which are usually used in cosmetics, quasi-drugs, pharmaceuticals, etc. Examples of the other appropriate ingredients used in combination with the glucosyladenosines in the external dermal agent of the present invention include the following ingredients including, for example, skin-whitening agents, antioxidants, anti-inflammatories, humectants, ultraviolet absorbing agents, emulsifiers, and thickeners.

Since the glucosyladenosines of the present invention are relatively stable against biogenic substances such as enzymes, they are hardly influenced by the other ingredients even when incorporated therewith, particularly, the glucosyladenosines have a lesser fear of being hydrolyzed by enzymes, etc., contained in natural ingredients such as plant extracts having the above activities, even when such natural ingredients are incorporated. Accordingly, there can be made into improved external dermal agents that exert the anti-wrinkle actions by the glucosyladenosines of the present invention along with the effects of the above active ingredients.

Examples of the skin-whitening agents include, for example, L-ascorbic acid and derivatives thereof, arbutin, kojic acid, ellagic acid, placenta extract, hydroquinone glycosides, tranexamic acid and derivatives thereof; resorcin and derivatives thereof such as resorcin, alkyl resorcinols such as 4-n-butylresorcinol, and salts thereof; glutathione; and plant extracts such as *Polygonum tinctorium* extract, *Glycyrrhiza uralensis* extract, *Scutellaria baicalensis* extract, *Ginkgo biloba* leaf extract, *Rosa multiflora* extract, *Magnolia* extract, *Paeonia lactiflora* extract, *Gardenia jasminoides* extract, *Salvia officinalis* extract, *Angelica sinensis* extract, *Iris* extract, and *Uncaria gambir* Roxb. extract. In particular, L-ascorbic acid 2-glucoside and tranexamic acid are preferable because they enhance the physiological activities of glucosyladenosines.

Examples of the antioxidants include, for example, butylhydroxytoluene, tocopherol, phytin, vitamin A and the like such as retinol and derivatives thereof; vitamin B and the like including vitamin $B_6$ hydrochloride, vitamin $B_6$ tripalmitate, vitamin $B_6$ dioctanoate, vitamin $B_2$ and derivatives thereof, vitamin $B_{12}$, and vitamin $B_{15}$ and derivatives thereof; vitamin C and the like including ascorbic acid and derivatives thereof; vitamin E and the like including α-tocopherol, β-tocopherol, δ-tocopherol, and vitamin E acetate; vitamin D and the like; glutathione, rutin, hesperidin, naringin and derivatives thereof; and plant extracts with antioxidative actions such as *Hypericum perforatum* extract, *Rosa multiflora* extract, *Scutellaria baicalensis* extract, tea extracts such as oolong tea, black tea, and green tea, and *Tricholoma matsutake* extract.

Examples of the anti-inflammatories include allantoin and derivatives thereof, glycyrrhetin and derivatives thereof such as glycyrrhetinic acid, glycyrrhizinic acid, allantoin glycyrrhizinate, glyceryl glycyrrhizinate, stearyl glycyrrhizinate, glycyrrhetinyl stearate, disodium 3-succinoyl glycyrrhetinate, dipotassium glycyrrhizinate, and monoammonium glycyrrhizinate; pantothenic acid and derivatives thereof; vitamin E and derivatives thereof; L-ascorbic acid and derivatives thereof such as L-ascorbic acid 2-glucoside, L-ascorbic acid dl-α-tocopherol phosphoric acid diester, L-ascorbic acid sulfate ester, ascorbyl dipalmitate, ascorbyl palmitate, stearyl ascorbic acid, L-ascorbic acid phosphate, and ethyl ascorbic acid; pyridoxine hydrochloride; menthol; biotin; camphor; turpentine; zinc oxide; azulene; guaiazulene and derivatives thereof; mefenamic acid and derivatives thereof; phenylbutazone and derivatives thereof; indomethacin and derivatives thereof; ibuprofen and derivatives thereof; ketoprofen and derivatives thereof; ε-aminocaproic acid; diclofenac sodium; diphenhydramine; tranexamic acid and derivative thereof; adrenocortical hormones such as dexamethasone, cortisone and esters thereof, hydrocortisone and esters thereof, prednisone, and prednisolone; antihistamines; and other plants and plant extracts such as *Rosa multiflora, Hypericum erectum, Phellodendron amurense, Glycyrrhiza uralensis, Nasturtium officinale, Symphytum officinale* L., *Salvia splendens, Lihospermum erythrohizon, Betula platyphylla, Camellia sinensis, Calendula officinalis* L., *Sambucus racemosa* subsp. *sieboldiana, Typha angustifolia, Sapindus mukorossi, Eucalyptus globulus* extract, *Brassica oleracea* var. *italica, Angelica sinensis* (Oliv.) Diels, *Perilla frutescens* var. *crispa, Matricaria recutita, Artemisia indica* var. *maximowiczii, Aloe vera, Daucus carota* L., powdered phellodendron bark, powdered myrica rubra bark, *Uncaria gambir* Roxb., *Hydrangea macrophylla* var. *thunbergii, Althea officinalis, Arnica, Echinacea purpurea* L. Moench, *Trillium apetalon, Scutellaria baicalensis* Georgi, *Hordeum vulgare, Citrus sinensis, Valeriana fauriei* Briq., *Matricaria recutita, Gardenia jasminoides, Sasa veitchii, Gentiana, Geranium thunbergii, Arctium lappa* L., *Zanthoxylum piperitum, Perilla frutescens* var. *crispa, Tilia miqueliana* Maxim., *Paeonia lactiflora, Hedera helix, Juniperus communis, Achillea millefolium, Cnidium officinale* Makino, *Swertia japonica, Salvia officinalis, Morus bombycis* Koidz., *Zizyphus jujuba, Thymus, Benincasa hispida, Prunus persica, Houttuynia cordata, Potentilla tormentilla, Petroselinum crispum, Mentha arvensis* L., *Urtica thunbergiana, Santalum album, Eriobotrya japonica, Aesculus hippocastanum, Vitis, Carthamus tinctorius, Paeonia suffruticosa, Tilia miqueliana* Maxim, *Amygdalus persica* L., *Rodgersia podophylla Rodgersia, Artemisia indica* var. *maximowiczii, Lavandula*, and *Rosmarinus officinalis* L.

Examples of the humectants include, for example, polyethylene glycol, propylene glycol, glycerin, 1,3-butylene glycol, hexylene glycol, xylitol, sorbitol, maltitol, chondroitin sulfate, hyaluronic acid, mucoitinsulfuric acid, charonic acid, atelocollagen, cholesteryl-12-hydroxystearate, sodium lactate, bile salts, dl-pyrrolidone carbonate, short-chain soluble collagen, diglycerin (EO) PO adduct; plant extracts such as *Rosa roxburghii* extract, *Achillea millefolium* extract, *Melilotus officinalis* extract, *Aloe vera* extract, *Swertia japonica* extract, *Sophora flavescens* extract, *Luffa cylindrica* (L.) Roem. extract, *Aesculus hippocastanum* L., *Saxifraga stolonifera, Thymus* extract, *Angelica acutiloba* extract, *Lilium* L. extract, *Gardenia jasminoides* extract, *Foeniculum vulgare* extract, *Lamium album* extract, *Menthaxpiperita* L.; and tranexamic acid.

Examples of the ultraviolet absorbing agents include, for example, those of benzoic acid ultraviolet absorbing agents such as p-aminobenzoic acid (abbreviated as "PABA", hereinafter), PABA monoglycerylester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA methyl ester; anthranilic acid ultraviolet absorbing agents such as homomethyl-N-acetyl-anthranilate; salicylic acid ultraviolet absorbing agents such as amyl salicylate, methyl salicylate, homomethyl salicylate, octyl salicylate, phenyl salicylate, benzyl salicylate, and p-isopropanol phenyl salicylate; cinnamic acid ultraviolet absorbing agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-ciano-3-phenyl cinnamate, 2-ethylhexyl-α-ciano-3-phenyl cinnamate, glycerylmono-2-ethylhexanoyl-diparamethoxycinnamate, and trimethoxy cinnamic acid methyl bis of (trimethyl siloxane) silyl isopentyl; and others such as 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotriazole 2-(2'-hydroxy-5'-t-octylphenyl) benzotriazole, 2-(2'-hydroxy-5'-t-methylphenyl)benzotriazole, dibenzalazine, ziani soil methane, 4-methoxy-4'-t-butyl dibenzoyl methane, 5-(3,3-dimethyl-2-norbornylidene)-3-pentane-2-on, and dimorpholinopyridazine, any one or more of which can be used.

Examples of the ultraviolet scattering agents include titanium oxide, particulate titanium oxide, zinc oxide, particulate zinc oxide, iron oxide, particulate iron oxide, cerium oxide, etc., in the form of a powder. These ultraviolet scattering agents are usually used in the form a needle-like, fusiform, spherical, or granular powder. Preferably used are particulate powders with a particle size of 01 μm or smaller. Hydrophobically-treated ultraviolet scattering agents, which have been treated with the following treatments, can be preferably used; silicon treatments with methyl hydrogen polysiloxane or silane coupling agents; metallic soap treatments; fluorine treatments with perfluoroalkyl phosphate diethanolamine or perfluoroalkyl silane; dextrin fatty acid ester treatments, etc.

Examples of the liquid oils and fats include, for example, avocado oil, camellia oil, turtle oil, *macadamia* nuts oil, corn oil, mink oil, olive oil, canola oil, egg-yolk oil, sesame oil, persic oil, wheat germ oil, rice germ oil, camellia oil, castor oil, linseed oil, safflower oil, cottonseed oil, *Perilla frutescens* var. *frutescens* oil, soybean oil, peanut oil, tea oil, Japanese torreya nuts oil, rice bran oil, *Paulownia furgasii* oil, Japanese tung oil, jojoba oil, triglycerine, etc.

Examples of the solid oils and fats include, for example, cacao butter, palm oil, horse fat, hardened palm oil, palm oil, beef fat, mutton suet, hardened beef fat, palm kernel oil, lard, beef bone fat, *Rhus succedanea* L. kernel oil, hardened oil, neat's foot oil, *Rhus succedanea* L., hydrogenated castor oil, etc.

Examples of the waxes include, for example, beeswax, candelilla wax, cotton wax, carnauba wax, bayberry wax, insect wax, whale wax, montan wax, rice bran wax, lanolin, capok wax, acetylated lanolin, liquid lanolin, corn wax, lanolin fatty acid isopropyl ester, hexyl laurate, hydrogenated lanolin, jojoba wax, hard lanolin, shellac wax, POE lanolin alcohol ether, POE lanolin alcohol acetate, POE cholesterol ether, polyethyleneglycol lanolin, POE hydrogenated lanolin alcohol ether, etc.

Examples of the hydrocarbon oils include, for example, liquid paraffin, ozokerite, scualane, pristane, paraffin, ceresin, squalene, petrolatum, micro crystalline wax, polyethylene wax, Fischer-Tropsch wax, etc.

Examples of the higher fatty acid include, for example, lauric acid, myristic acid, palmitic acid, stearic acid, behenic acid, oleic acid, undecylenic acid, tall oil acid, linolic acid, linoleic acid, eicosapentaenoic acid (EPA), docosahexaenoic acid (DHA), etc.

Examples of the higher alcohols include, for example, linear alcohols (for example, lauryl alcohol, cetyl alcohol, stearyl alcohol, behenyl alcohol, myristyl alcohol, oleyl alcohol, cetostearyl alcohol, etc.); branched alcohols (for example, glycerin monostearyl ether (batyl alcohol), 2-decyltetradecynol, lanolin alcohol, cholesterol, phytosterol, hexyldodecanol, octyldodecanol, etc.), etc.

Examples of the synthetic ester oils include, for example, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, monoisostearate-N-alkylglycol, neopentyl glycol dicaprate, diisostearyl malate, glyceryl di-2-heptylundecanoate, trimethylolpropane tri-2-ethylhexanoate, trimethylolpropane triisostearate, pentaerythritol tetra(2-ethylhexanoate), tri-2-ethylhexanoate glyceryl, glyceryl tri(2-ethylhexanoate), glyceryl trioctanoate, glycery triisopalmitate, trimethylolpropane triisostearate, cetyl 2-ethylhexanoate, 2-ethylhexyl palmitate, glyceryl trimyristate, tri-2-heptylundecanoate acid glycerides, castor oil fatty acid methyl ester, oleyl oleate, acetoglyceride, 2-heptyl undecyl palmitate, isobutyl adipate, N-lauroyl-L-glutamic acid-2-octyldodecylester, di-2-heptylundecyl adipate, ethyl laurate, di(2-ethylhexyl)sebacate, 2-hexyldecyl myristate, 2-hexyldecyl palmitate, 2-hexyldecyl adipate, 2-ethylhexyl succinate, triethyl citrate, polyoxyethylene-polyoxypropylene random polymer methyl ether, etc.

Examples of the silicon oils include, for example, chain polysiloxane (for example, dimethylpolysiloxane, methylphenylpolysiloxane, diphenylpolysiloxane, etc.); cyclic polysiloxane (for example, octamethylcyclotetrasiloxane, decamethylcyclopentasiloxane, docecamethylcyclohexasiloxane, etc.); silicon resins with three-dimensional network; silicon rubber; and denatured polysiloxanes (for example, amino-denatured polysiloxane, polyether-denatured polysiloxane, alkyl-denatured polysiloxane, fluorine-denatured polysiloxane, etc.) or the like.

Examples of others include lower alcohols such as ethanol; acyl sarcosinates (for example, sodium lauroyl sarcosinate); organic acids such as citric acid, malic acid, tartaric acid, lactic acid; vitamins such as vitamin H, pantothenic acid, pantethine; nicotinic-acid amide; benzyl nicotinate; γ-orizanol; allantoin; glycyrrhizic acid (salts); glycyrrhetinic acid and derivatives thereof; hinokitiol; bisabolol; eukalypton; thymol; inositol; saponins such as saikosaponin, carrot saponin, sponge gourd saponin, saponin of *Sapindus mukurossi* Gaertn; medicaments such as pantothenyl ethyl ether, ethynylestradiol, cepharanthine, placenta extract; plant extracts and crude drugs such as *Rumex japonicus, Malva, Picea jezoensis* (Sieb. et Zucc.) Carr. var. *hondoensis* (Mayr) Rehd., *Equisetum arvense, Lilium, Artemisia* indica var. *maximowiczii, Chamaecyparis pisifera, Crataegus oxyacantha* (*C. monogyna*) extract, *Thymus quinquecostatus* extract, *Nymphaea* extract, *Tamarix chinensis* extract, *Potentilla tormentilla* extract, *Mentha×piperita* L.; royal jelly extract; pigments; non-ionic surfactants such as sorbitan monolaurate, sorbitan monopalmitate, sorbitan sesquioleate, sorbitan trioleate, polyoxyethylene sorbitan monolaurate, polyoxyethylene sorbitan monostearate, poly(ethylene glycol)monooleate, polyoxyethylene alkyl ether, polyglycol diether, lauroyldiethanolamide, fatty acid isopropanolamide, maltitol hydroxy fatty acid ether, alkylated polysaccharides, alkylglucosides, sugar ester; cationic surfactants such as stearyl-trimethylammonium chloride, benzalkonium chloride, lauryl amine oxide; anionic surfactants such as sodium palmitate, sodium laurate, sodium laurylate, potassium lauryl sulfate, alkyl sulfate triethanolamine ether, turkey red oil, linear dodecylbenzenesulfonic acid, castor oil hydrogenated ethoxylated polymer with maleic acid, acyl methyl taurate; ampholytic surfactants; neutralizers; pH-regulators; buffers; antioxidants such as 5-tocopherol and butylhydroxytoluene; and antiseptics such as phenoxyethanol, paraben, alkane diols, photosensitizer 201. In addition, the following other ingredients can be appropriately incorporated: Sequestering agents such as edetate disodium, edetate trisodium, edetate tetrasodium, sodium citrate, sodium polyphosphate, sodium metaphosphate, gluconic acid; caffeine; tannin; verapamil; tranexamic acid and derivatives thereof; polyphenols including rutin, hesperidin, anringin, and derivatives thereof; *Glycyrrhiza* extract; glabridin; *Pyracantha* fruit extract extracted with hot water; carnitine; Coenzyme $Q_{10}$, crude drugs; tocopherol acetate, hydroxy decenoic acid, glycyrrhizic acid, and their derivatives and salts; saccharide such as glucose, fructose, mannose, sucrose, α,α-trehalose, saccharide derivatives of α,α-trehalose, cyclic tetrasaccharides, dextrins, cyclodextrins, branched dextrins, starches, branched dextrins, and pullulan; photosensitizers such as photosensitizer 101, photosensitizer 301, photosensitizer 401; flavors; pigments/dyes, etc.

The external dermal agent of the present invention includes cosmetics, pharmaceuticals, and quasi-drugs; and the formulation of the agent includes appropriate forms of aqueous solutions, solubilizations, emulsifications, oil liquids, gels, pastes, ointments, aerosols, two layer systems of water/oil, three layer systems of water/oil/powder, etc. Further, the agent includes those which are supported on sheet- or powder-bases.

The term external dermal agent as referred to in the present invention means those which are directly applied to the epidermis of the skin of the face, the body, or the like for the purpose of preventing rough skin, blemishes and wrinkles, inflammation, and ageing; or those which may affect on the skin when contacted with the skin upon use; cosmetics, quasi-drugs and pharmaceuticals including skin-care cosmetics, makeup cosmetics, bodycare cosmetics, oral-care cosmetics, and perfume/fragrance cosmetics such as cosmetic soaps, face washes, creams/milky lotions in general, cosmetic lotions, eau de cologne, lotions, cosmetic oils, white face powders/powders, foundations, rouges/pencils, eye creams/eye shadows/mascaras, perfumes, suntan/sunburn-preventing creams, suntan/sunburn-preventing lotions, suntan/sunburn-preventing oils, eyeliners, lipsticks, chapsticks, dentifrices, bath products, and therapeutic agents for diseases. The term external dermal agent also includes pharmaceuticals and quasi-drugs which are used by applying or attaching to the skin or mucosa such as ointments, paps/cataplasms, films, etc.; and those such as cachous contacted directly with the oral mucosa when used.

For reference, the glucosyladenosines as the effective ingredients of the external dermal agent of the present invention should not be restricted to those which are produced by specific methods and means, however, enzymatic methods with glycosyltransferases are advantageous when considering economy. For example, the glucosyladenosines can be produced on a larger scale and in a lesser cost by an enzymatic method using an enzyme with a glycosyltransferring activity such as cyclomaltodextrin glucanotransferase (CGTase), α-glucosidase, amylase, α-isomaltosyl-glucosaccharide-forming enzyme (see, for example, International Patent Publication No. WO02/10361), isomaltosyl-transferring enzyme (see, for example, International Patent Publication No. WO01/90338), α-glucosyltransferase (International Patent Publication No. WO2008/136331), and α-amylase that hydrolyzes starch, catalyzes the transferation of glycosyl groups to form cyclodextrin, and acts on pullulan to form panose (International Patent Publication No. WO2008/136331). Particularly, in the case of using the α-glucosyltransferase disclosed in International Patent Publication No. WO2008/136331, 5'-glucosyl-adenosine with a relatively high water-solubility can be obtained in a relatively high yield. While, when using CGTase, glucosyladenosines with a higher composition ratio of 3'-glucosyl-adenosine than that prepared with α-glucosyltransferase can be obtained in a relatively high yield.

By allowing α-glucosyltransferase or CGTase having a glycosyltransferring activity to act on a solution containing amylaceous substance and adenosine, one or more molecules of D-glucoses are transferred to the hydroxyl group at the C-3' or C-5' position of adenosine to form 3'- or 5'-glucosyladenosine, where one molecule of D-glucose binds to the above hydroxyl group at the C-3' or C-5' position, where one molecule of D-glucose binds to the above hydroxyl group at the C-3' or C-5' position; and to form compounds, where two or more molecules of D-glucoses are bound to the C-3' or C-5' position, for example, 3'-glycosyladenosines such as 3'-maltosyladenosine and 3'-maltotoriosyladenosine, and 5'-glycosyladenosines such as 5'-maltosyladenosine and 5'-maltotriosyladenosine are formed.

These α-glucosyltransferase and CGTase are usually added to an aqueous solution, prepared by dissolving amylaceous substance and adenosine to give an amylaceous substance concentration of 1 to 40 w/v %, in an amount of 1 to 2,000 units/g amylaceous substance, preferably, 1 to 1,000 units/g amylaceous substance; and allowing the resulting mixture to an enzymatic reaction at a pH of about 3 to about 10 and a temperature of 30 to 70° C. for at least six hours, preferably, about 12 to about 96 hours.

The mass ratio of amylaceous substance to adenosine in a solution is usually set to 1:2 to 20:1 on a dry solid basis (d.s.b.), preferably, 1:1 to 10:1. When the ratio of amylaceous substance exceeds the above range, glucosyl transfer to adenosine well proceeds but the adenosine yield is restricted by an initial concentration of adenosine, resulting in a low yield. On the contrary, when the ratio of adenosine exceeds the above range, intact adenosine remains in a large quantity, and this is not preferable for an industrial scale production. Accordingly, the ratio of the above range is regarded as best.

In addition to the above α-glucosyltransferase and CGTase, in the case of using isoamylase as a debranching enzyme, such isoamylase should preferably be allowed to act on amylaceous substance under the condition of being coexisted with α-glucosyltransferase and CGTase in a solution containing adenosine and amylaceous substance. Varying depending on the optimum temperature and the pH of isoamylase, such isoamylase is usually added in an amount of 200 to 2,500 units/g amylaceous substance and is preferably enzymatically reacted at a temperature of 55° C. or lower. When pullulanase is used as a debranching enzyme, such pullulanase can be used in accordance with the above isoamylase.

After passing through the enzymatic reactions with α-glucosyltransferase and/or CGTase along with a debranching enzyme, the resulting reaction mixture is heated to inactivate the remaining enzymes to suspend the enzymatic reactions, and then the enzymatic reaction solution is subjected to the action of glucoamylase. By the action of glucoamylase, most of the chains consisting of two or more molecules of D-glucose bound to the hydroxyl groups at the C-3' and/or C-5' positions of adenosine are cleaved to transform glycosyladenosines into 3'-glucosyladenosine and/or 5'-glucosyladenosine with an increased yield. The resulting reaction solution with an increased content percentage of 3'-glucosyladenosine and/or 5'-glucosyladenosine can be in usual manner decolored and filtered with an activated charcoal, etc., and subjected to column chromatography using ion-exchange resins, synthetic absorption resins, and porous resins to purify glucosyladenosines in the solution. If necessary, 3'-glucosyladenosine and/or 5'-glucosyladenosine can be increased in their purity by using reverse-phase chromatography, etc., and they can be arbitrarily respectively isolated and purified before use. Solutions containing these glucosyladenosines can be used intact as materials for the external dermal agent of the present invention and, if necessary, they can be concentrated before use and dried by an appropriate method such as drying in vacuo or spray drying, and then pulverized, if necessary.

According to cost distribution to amylaceous substance in terms of the production cost of glucosyladenosines, starch is desirably used as a material, and, in such case, the polymerization degree of glucose in liquefied starch should be adjusted, and starch-debranching enzymes such as isoamylase (EC 3.2.1.68) and pullulanase (EC 3.2.1.41) can be advantageously used in combination to cleave debranching sites. Among these starch-debranching enzymes, isoamylase is particularly preferable because of its enzyme activity and substrate specificity. Examples of such starch include potato starch, sweet potato starch, tapioca starch, corn starch, wheat starch, etc. Partial starch hydrolyzates such as dextrin can be used and amylaceous substances, which substantially do not have an intramolecular debranching structure and have a uniform glucose polymerization degree, for example, cyclomaltodextrin, cycloamylose, synthetic amylose, etc., can be arbitrarily used.

Glucoamylase, used for cleaving the chains consisting of two or more molecules of D-glucose bound to the hydroxyl group at the C-3' and/or C-5' positions of adenosine, should not be restricted to those which are derived from specific sources and have specific purities, and commercialized ones can be used: "GLUCOZYME #20000", a product name of a commercialized glucoamylase preparation, i.e., an enzyme preparation derived from a microorganism of the genus *Rhizopus*, commercialized by Nagase ChemteX Corporation, Osaka, Japan; and "GLUCZYME", a product name of an enzyme preparation derived from a microorganism of the genus *Aspergillus* or *Rhizopus*, commercialized by Amano Pharmaceutical Company, Aichi, Japan, can be used.

The following explain the present invention in more detail.

Experiment 1

Preparation of Glucosyladenosine Using α-glucosyltransferase

<Experiment 1-1: Preparation of α-Glucosyltransferase>
According to the method in Experiment 5 of International Patent Publication No. WO2008/136331, *Bacillus circulans* PP710 strain, which has been deposited with International Patent Organism Depositary (IPOD) National Institute of Technology and Evaluation (NITE) (former International Patent Organism Depositary, National Institute of Advanced Industrial Science and Technology), Tsukuba Central 6, 1-1, Higashi 1-chome, Tsukuba-shi, Ibaraki-ken, 305-8566 Japan, under the accession number of FERM BP-10771, was inoculated to a liquid culture medium consisting of 1.5 w/v % "PINEDEX #4", a product name of a partial starch hydrolyzate commercialized by Matsutani Chemical Industry Co., Ltd, Hyogo, Japan, 0.5 w/v % "POLYPEPTONE", a product name of an yeast extract commercialized by Nihon Pharmaceutical Co., Ltd., Tokyo, Japan, 0.1 w/v % "YEAST EXTRACT S", a product name of an yeast extract commercialized by Nihon Pharmaceutical Co., Ltd., Tokyo, Japan, 0.1 w/v % dipotassium phosphate, 0.06 w/v % sodium phosphate dihydrate, 0.05 w/v % magnesium sulfate heptahydrate, 0.001 w/v % manganese sulfate pentahydrate, 0.001 w/v % ferrous sulfate heptahydrate, and water; and cultured in a fermentor for about 24 hours. After the culturing, the culture was centrifuged to collect a culture supernatant, which was then admixed with ammonium sulfate to give 80% saturation, and allowed to stand at 4° C. for 24 hours to effect salting. The precipitate was collected by centrifugation, dissolved by the addition of 20 mM acetate buffer (pH 6.0), and dialyzed against the same buffer, followed by concentrating the dialyzed solution into a concentrated crude enzyme solution. The crude enzyme solution had about 1,300 units/ml of α-glucosyltransferase activity. The concentrated crude enzyme solution also had about 140 units/ml of amylase activity.

The above α-glucosyltransferase activity is assayed as follows: Maltose is dissolved in 20 mM acetate buffer (pH 6.0) to give a final concentration of 1 w/v % for use as a substrate solution. To five milliliters of the substrate solution 0.5 ml of an enzyme solution is added, and the mixture is enzymatically reacted at 40° C. for 30 min. A half milliliter of the enzymatic reaction solution is mixed with five milliliters of 20 mM acetate buffer (pH 7.0), heated in a boiling water for 10 min to suspend the enzymatic reaction, followed by quantifying the glucose content in the enzymatic reaction solution according to conventional glucose oxidase method and calculating the glucose content formed by the enzymatic reaction. One unit activity of α-glucosyltransferase is defined as the enzyme amount that forms one micromole of glucose per minute under the above conditions. The activity of the coexisting amylase was defined as follows: "AMYLOSE EX-I", a product name of a short-chain amylose with an average polymerization degree of 17, commercialized by Hayashibara Biochemical Laboratories Inc., Okayama, Japan, was dissolved in 50 mM acetate buffer (pH 6.0) containing 1 mM calcium chloride to give a final concentration of 1 w/v % for use as a substrate solution. Two milliliters of the substrate solution was admixed with 0.2 ml of an enzyme solution and subjected to an enzymatic reaction at 35° C. for 30 min. To 0.2 ml of the resulting enzymatic reaction solution was added eight milliliters of 0.02 N sulfuric acid solution to suspend the enzymatic reaction, admixed with 0.2 ml of 0.1 N iodine solution, incubated at 25° C. for 15 min, and measured for absorbance at a wavelength of 660 nm. An enzymatic reaction solution at a reaction time 0 was similarly measured for determining an iodine color reduction per a prescribed period of time. One unit of amylase activity was defined as 10-folds of the enzyme amount that reduces the absorbance at 660 nm (iodine coloration) of 20 mg of a short-chain amylose under the above conditions by 10%.

<Experiment 1-2: Preparation of Glucosyladenosine>

Adenosine, a special grade reagent commercialized by Wako Pure Chemical Industries, Tokyo, Japan, was dissolved in 0.3 N hydrochloric acid to give a concentration of 10% by mass. Forty milliliters of a 10% by mass of adenosine solution and 12 g of "PINEDEX #1", a product name of a dextrin with a solid content of about 92.3% by mass, commercialized by Matsutani Chemical Industry Co., Ltd, Tokyo, Japan, were added to 336 ml of 50 mM acetate buffer (pH 6.0) containing 2 mM $CaCl_2$, mixed by stirring, admixed with nine milliliters of an enzyme solution, which had been prepared by diluting the concentrated crude enzyme solution that had had been prepared in Experiment 1-1 with 50 mM acetate buffer (pH 6.0) to give an α-glucosyltransferase activity of 20 units/ml, mixed by stirring, and enzymatically reacted at 50° C. for 24 hours. After completion of the enzymatic reaction, the resulting enzymatic reaction solution was admixed with 1 N hydrochloric acid, and the mixture was adjusted to pH 3.5, admixed with "XL-4", a product name of a glucoamylase containing 3,800 units/ml, commercialized by Nagase ChemteX Corporation, Osaka, Japan (former Nagase Biochemical Co., Ltd., Kyoto, Japan), in an amount of 1,000 units/g solid dextrin, enzymatically reacted at 50° C. for 24 hours, and heated at 100° C. for 10 min to suspend the enzymatic reaction. The resulting enzymatic reaction solution was fed to a column (100 mm×ø41 mm) packed with an activated charcoal at a flow rate SV=3 (5 ml/min) to absorb glucosyladenosine to the column, and the column was washed with deionized water in a volume of 5-folds of the wet charcoal volume and 20% v/v ethanol solution in a volume of 3-folds of the wet charcoal volume, and eluted with 40 v/v % ethanol solution. The eluate was fractionated by 50 ml, and fractions with an ultraviolet absorption (260 nm) level of 0.15 or higher were collected. The collected fractions were pooled, concentrated by a rotary evaporator, and fed to a preparative high-performance liquid chromatography (HPLC) with an ODS column to collect a main peak of the eluted fractions of glucosyladenosine. The preparative separation of the main peak on HPLC with the ODS column was performed in twice to obtain a specimen containing at least 99% by mass of glucosyladenosine, d.s.b., in a total amount of about 0.8 g. The preparative HPLC was conducted under the following conditions:

<Conditions for Preparative HPLC>
Apparatus: Shimadzu Shodex RI-102 (a detector), LC-10AD (a pump), SIL-10ADvp (an autosampler), C-R7Aplus (a recorder);
Column: "YMC-Pack R & D ODS-A", an ODS column, 020 mm×250 mm, commercialized by YMC Co., Ltd., Kyoto, Japan;
Mobile phase: {20 mM Acetic acid-ammonium acetate buffer (pH 3.5)}/(methanol)=84/16 (v/v); Detection: RI;
Flow rate: 3.0 ml/min;
Column temperature: 35° C.

Experiment 2

Preparation of Glucosyladenosine by CGTase

Adenosine (a special grade reagent commercialized by Tokyo Chemical Industry Co., Ltd. (TCI), Tokyo, Japan), and "PINEDEX #1", a dextrin commercialized by Matsutani Chemical Industry Co., Ltd, Hyogo, Japan, were dissolved in 10 mM sodium acetate solution (pH 5.5) to give respective concentrations of 1 w/v % and 10 w/v %, heated to 50° C., and dissolved completely by stirring. To the resulting solution was added a CGTase, produced by Hayashibara Biochemical Laboratories Inc., Okayama, Japan, derived from a microorganism of the species *Geobacillus stearothermophilus* (*Bacillus stearothermophilus* as in an old classification) Tc-91, which had been transferred from FERM P-2225 into an international deposition and has been deposited with International Patent Organism Depositary in National Institute of Advanced Industrial Science and Technology, Tsukuba Central 6, 1-1, Higashi 1-chome, Tsukuba-shi, Ibaraki-ken, 305-8566 Japan, disclosed in Japanese Patent Kokai No. 63189/75 (Japanese Patent Kokoku No. 27791/78), in an amount of 1,000 units/g dextrin; enzymatically reacted at 50° C. for 24 hours; heated at 100° C. for 15 min to inactivate the remaining CGTase; admixed with "GLUCOZYME #20000", a product name of a glucoamylase with 20,000 units/g, commercialized by Nagase ChemteX Corporation, Osaka, Japan, in an amount of 2,600 units/g dextrin, and enzymatically reacted at 50° C. for 24 hours. The enzymatic reaction solution was heated at 100° C. for 10 min and centrifuged at 11,500 rpm to collect a supernatant. The resulting supernatant was fed to a column, 120 mm×ø41 mm, packed with an activated charcoal in a volume of 150 ml, at an SV=3 (5 ml/min) to adsorb glucosyladenosine to the column, followed by washing the column with deionized water in a volume of 7-folds of the wet charcoal volume and 20 v/v % ethanol solution in a volume of 6-folds of the wet charcoal volume and eluting the adsorbed ingredients with 40 v/v % ethanol solution in a volume of 16-folds of the wet charcoal volume. The eluate was fractionated by 50 ml, and the fractions with an ultraviolet absorption (260 nm) of 0.15 or higher were collected. The collected fractions were pooled, concentrated, and fed to a preparative HPLC column with an ODS column to collect a main peak containing glucosyladenosine. The collected main peak fraction was fed to an activated charcoal column to adsorb glucosyladenosine and to effect desalting, followed by elution with 40 v/v % ethanol and concentrating the eluate with a rotary evaporator to collect eluted fractions with glucosyladenosine. The preparative HPLC was conducted under the same conditions as in the above Experiment 1-2, except for using 20 mM acetic acid-ammonium acetate buffer (pH 3.5)/methanol in a volume ratio of 82/18 (v/v) as a mobile phase and a column temperature of 40° C., to prepare about 1.6 g of a specimen containing at least 99% by mass of glucosyladenosine, d.s.b. The main peak of the glucosyladenosine, which had been eluted from the preparative HPLC with an ODS column, was eluted at a different retention time from that of the main peak of the glucosyladenosine that had been eluted in Experiment 1-2. The fact that the main peak contained glucosyladenosine was also confirmed by the measurement for molecular weight determined on conventional mass spectrum (MS) analysis.

In Experiments 1-2 and 2, the structures of two types of glucosyladenosines prepared by the preparative HPLC with an ODS column were determined on conventional NMR analysis. The carbon chemical shifts of the two types glucosyladenosines based on the NMR analysis are shown in Table 1 along with that of adenosine. NMR Analysis was conducted by the following conditions. Table 1 also shows the carbon chemical shifts of adenosine obtained from the spectrum data base system for organic compounds opened by The National Institute of Advanced Industrial Science and Technology (AIST) (SDBS; http://riodb01.ibase.aist.go.jp/sdbs/cgi-bin/direct_frame_top.cgi).

<Conditions for NMR Analysis>
Apparatus: "JNM-AL300", a product name of JEOL Ltd., Tokyo, Japan, $^1$H: 300.4 MHz, $^{13}$C: 75.45 MHz;

Medium: Deuterium water (0.6 ml);
Internal standard: Sodium 3-(trimethylsilyl)-1-propanesulfonate (TPS);
Cumulated number: $^1$H-NMR 128 times, $^{13}$C-NMR 4,000 times, DEPT 400 times, H—H COSY 32 times, H—C COSY 36 times; and
Sample: 20 mg.

TABLE 1

| | | | δc (ppm) | | |
|---|---|---|---|---|---|
| | | Carbon No. | Adenosine* | Glucosyladenosine prepared in Experiment 1-2 | Glucosyladenosine prepared in Experiment 2 |
| Adenosine | Adenine | 1 | 155.5 | 157.2 | 157.6 |
| | | 2 | 152.1 | 154.6 | 154.5 |
| | | 3 | 149.0 | 150.6 | 150.7 |
| | | 4 | 141.4 | 142.4 | 142.9 |
| | | 5 | 119.6 | 120.5 | 121.3 |
| | Ribose | 1' | 88.9 | 89.7 | 90.6 |
| | | 2' | 74.3 | 76.6 | 75.6 |
| | | 3' | 71.1 | 71.8 | 79.1 |
| | | 4' | 86.3 | 85.4 | 86.6 |
| | | 5' | 62.0 | 69.0 | 63.7 |
| Glucose | Glucose | 1" | — | 100.7 | 101.8 |
| | | 2" | — | 73.6 | 73.9 |
| | | 3" | — | 71.8 | 71.9 |
| | | 4" | — | 74.5 | 75.1 |
| | | 5" | — | 74.5 | 75.1 |
| | | 6" | — | 62.8 | 62.9 |

*When DMSO is used as a solvent.

As evident from Table 1, since the δc values of the C-5' position of ribose for the glucosyladenosine prepared in Experiment 1-2 and those of the C-3' position of ribose for the compound prepared in Experiment 2 were shifted, these compounds were respectively identified as 5'-glucosyladenosine and 3'-glucosyladenosine.

<Solubility of Glucosyladenosines in Water>

As a basic property, the solubilities in water of the glucosyladenosines of the present invention were compared with that of adenosine. The 5'-glucosyladenosine prepared in Experiment 1-2 and the 3'-glucosyladenosine prepared in Experiment 2 were determined for solubility in water, and they were compared with that of adenosine. One hundred milligrams of 5'-glucosyladenosine or 3'-glucosyladenosine (these compounds may be collectively called glucosyladenosines, hereinafter) was dissolved in 500 μl of pure water at an ambient temperature (25° C.). While, five milligrams of adenosine was dissolved in 500 μl of pure water at an ambient temperature (25° C.). These solutions were allowed to stand at 25° C. for one day, and a supernatant was separated from a remaining undissolved precipitate by centrifugation, filtered with "ULTRAFREE 0.5 Biomax-5 Membrane", a product name of an ultra-filter commercialized by Nihon Millipore K.K., Tokyo, Japan, diluted with the mobile phase, and membrane filtered with "Millex-LH", a product name of a filter with a pour size of 0.45 μm, commercialized by Nihon Millipore K.K., Tokyo, Japan. The filtrate was fed to HPLC under the following conditions, followed by determining the respective contents of glucosyladenosines and adenosine based on the peak areas appeared on a chromatogram by an ultraviolet detector, and calculating their concentrations as maximum dissolved concentrations at an ambient temperature (25° C.). The same samples were allowed to stand at a 4° C. cold room for one month and centrifuged, followed by quantifying the contents of glucosyladenosines and adenosine in the resulting supernatants similarly as above to determine their maximum dissolved concentrations at 4° C. The results are in Table 2.

<Conditions for HPLC Analysis>
Apparatus: SHIMADZU UV-VIS DETECTOR SPD-10AV (a detector), LC-10AT (a pump), C-R8A (a recorder), and SIL-20AC (an autosampler);
Column: "YMC-Pack ODS-A", a product name of an ODS column, ø4.6 mm×250 mm, commercialized by YMC commercialized by YMC Co., Ltd., Kyoto, Japan;
Mobile phase: (0.1 v/v % aqueous acetic acid solution)/(methanol)=96/4 (v/v),
Detection wavelength: 260 nm,
Flow rate: 1.0 ml/min,
Injection volume: 20 μl, and
Column temperature: 40° C.

TABLE 2

| | Maximum dissolved concentration (w/v %) | |
|---|---|---|
| Test sample | 4° C. | 25° C. |
| Adenosine | 0.4 | 0.8 |
| 5'-Glucosyladenosine | 15.7< | 16.1< |
| 3'-Glucosyladenosine | 2 | 2 |

As evident from Table 2, adenosine only dissolved in water at a concentration of 0.8 w/v % at an ambient temperature (25° C.), while 3'-glucosyladenosine dissolved in water at a concentration of up to 2 w/v % and more increased its solubility in water than that of adenosine. 5'-Glucosyladenosine dissolved in water at a concentration of over 16.1 w/v % at the ambient temperature and distinctly increased its solubility in water than that of adenosine. Although adenosine only dissolved in water at a concentration of 0.4 w/v % of, 3'-glucosyladenosine dissolved in water at a concentration of up to 2.0 w/v % and more increased its solubility in water than that of adenosine. 5'-Glucosyladenosine dissolved in water with 4° C. at a concentration of over 15.7 w/v % and distinctly more increased its solubility in water than that of adenosine. These results indicate that, when used in producing external dermal agents using hydrophilic media, 3'- and 5'-glucosyladenosines can be, for example, mixed in a solution form without a fear of causing precipitation after being insolubilized when mixing, indicating that they have an appropriate processability in producing homogeneous external dermal agents.

Experiment 4

Sustainability of Glucosyladenosines

<Experiment 4-1: Resistance to Adenosine Deaminase>

Adenosine has been confirmed to be promptly hydrolyzed into inosine and hypoxanthine by adenosine deaminase (ADA) intrinsically present in living bodies. To examine the possibility of sustainably exerting effects by glucosyladenosines as adenosine glycosides, a test for confirming whether 5'- and 3'-glucosyladenosines are hydrolyzed in living bodies was conducted using a cell lysate of a normal human fetal fibroblast as a source for an adenosine metabolism-relatedenzyme. "NHDF cells", a normal human fetal fibroblast, commercialized by Kurabo Industries, Osaka, Japan (called "NHDF cells", hereinafter), which had been diluted with "Dulbecco's Modified Eagle Medium "Nissui" (abbreviated as "NHDF", hereinafter), a product name of a Dulbecco's Medium Essential Medium, commercialized by Nissui Pharmaceutical Co., Ltd., Tokyo, Japan, containing 10 v/v % fetal calf serum albumin (called "FCS", hereinafter) was inoculated to 150 cm$^2$ culture flasks (commercialized by Corning, N.Y., USA) in a cell amount of $1.5 \times 10^6$ cells/20 ml/flask, and cultured for four days. After removing each culture supernatant, the resulting cells were treated with "Trypsin-EDTA", a product name of 0.05% by mass of trypsin/EDTA solution, commercialized by Gibco, NY., USA, followed by collecting the cell suspensions from each flask. The cell suspensions were pooled, centrifuged to remove supernatants, and admixed with 10 mM Tris-HCl buffer (pH 7.5), as a lysis buffer, to which had been added "Complete, EDTA-free, tablets", a protease inhibitor cocktail, commercialized by Hoffmann-La Roche Ltd., Basel, Switzerland, to suspend NHDF cells at a cell concentration of $4.0 \times 10^6$ cells/ml. The cell suspension was ultrasonically treated with "BRANSON SINIFIER CELL DISROPTOR 185" thrice (30 sec×twice for each) for cell disruption, centrifuged at 15,000 rpm for five minutes to collect supernatants as a cell lysate. 0.9 ml of the cell lysate and 0.1 ml of phosphate buffered saline (PBS), which had been prepared by dissolving either the 5'-glucosyladenosine that had had been prepared in Experiment 1-2 or the 3'-glucosyladenosine that had had been prepared in Experiment 2 to give a concentration of 5 mM, were mixed, stirred, and allowed to react at 37° C. Reaction solutions at reaction times 0, 1, 7 and 24 hours after initiating the reaction were collected, treated with the same method as in Experiment 3, and quantified for adenosine and glucosyladenosines by an HPLC method. Relative values for concentrations of these compounds at respective reaction times were calculated when the concentration at the reaction initiation for each compound was regarded as 100%, and they are shown in Table 3 as residual percentages of adenosine or glucosyladenosines.

TABLE 3

| Test sample | Remaining percentage (%) Reaction time (hour) | | | |
| --- | --- | --- | --- | --- |
| | 0 | 1 | 7 | 24 |
| Adenosine | 100 | 53 | 0 | 0 |
| 5'-Glucosyladenosine | 100 | 101 | 100 | 96 |
| 3'-Glucosyladenosine | 100 | 95 | 86 | 17 |

As evident from Table 3, adenosine was promptly hydrolyzed by the enzyme contained in the cell lysate and completely disappeared within seven hours of the enzymatic reaction. At least 90% of 5'-glucosyladenosine remained even at 24 hours reaction. While at least 80% of 3'-glucosyladenosine remained at seven hours of reaction and 17% of which remained at 24 hours of reaction. These results indicate that adenosine is susceptible to hydrolysis in living bodies within a relatively short period of time to lose its functions, while 3'- and 5'-glucosyladenosines are unsusceptible to the action of enzymes present intrinsically in living bodies, such as adenosine deaminase (ADA) and α-glucosidase, and they remain for a relatively longer period of time than adenosine and exert their functions. For reference, when reacted with cell lysate of NHDF cells, 5'- and 3'-glucosyladenosines form inosine and hypoxanthine and such reaction was inhibited by α-glucosidase (not shown in data), and therefore it was judged that adenosine glycosides are hydrolyzed by an intracellular α-glucosidase into adenosine and glucose, which are then hydrolyzed into inosine and hypoxanthine similar to adenosine.

<Experiment 4-2: Residual Property in Three-Dimensional Skin Model>

To judge the sustainability of the effects of the glucosyladenosines of the present invention, residual properties in three-dimensional skin environment were examined. "EPI Assay Medium", a product name of EPI100 assay medium commercialized by Kurabo Industries Ltd., Okayama, Japan, was added to "12-WELL MULTI-MICROPLATE", a product name of 12-well plate commercialized by Becton, Dickinson and Company, NJ, USA, in a volume of 0.33 ml/well; and "EPI-200 Kit", a product name of a three-dimensional skin model cup, commercialized by Kanebo Cosmetics Inc., Tokyo, Japan, was transferred to each well. After incubating at 37° C. for three hours in a 5 v/v % CO$_2$ condition, the skin model cups were transferred to "6-WELL MULTIWELLPLATE", a product name of a 6-well plate, commercialized by Becton, Dickinson and Company, NJ, USA, supplemented with "Dulbecco's Modified Eagle Medium "Nissui", a product name of a DMEM medium, commercialized by Nissui Pharmaceutical Co., Ltd., Tokyo, Japan, in an amount of 0.9 ml/well. 5'-Glucosyladenosine prepared by the method in Experiment 1-2,3'-glucosyladenosine prepared by the method in Experiment 2, or adenosine was dissolved in 30% ethanol to give a final concentration of 0.1%, and 0.1 ml of each of the resulting solutions was added to each of the skin model cup. After incubating at 37° C. for 24 hours in a 5% CO$_2$ condition, sample solutions (media in wells) were collected, subjected to ultrafiltration with "ULTRAFREE 0.5 BIOMAX-5 MEMBRANE", a product name of membrane commercialized by Nihon Millipore K.K., Tokyo, Japan, and diluted with the mobile phase. The diluent was subjected to HPLC under the following conditions and determined for the contents of 5'- and 3'-glucosyladenosines with an alternatively prepared standard curve. Table 4 shows the residual contents of compounds after three-dimensional skin permeation and the production yields of inosine and hypoxanthine.

<Conditions for HPLC Analysis>

Apparatus: an HPLC Pump, MODEL 510; a pump controller, MODEL 680; an autoinjector, MODEL 712; a detector, MODEL 2487; a data processing (quantity calculation), EMPOWER 2 SOFTWARRE, commercialized by Nihon Millipore K.K., Tokyo, Japan;

Column: "YMC-PACK ODS AQ-303", a product name of an ODS column, ⌀4.6 mm×250 mm, commercialized by YMC Co., Ltd., Kyoto, Japan;

Mobile phase: {20 mM Acetic acid-ammonium acetate buffer (pH 3.5)}/(methanol)=92/8 (v/v);

Detection wavelength: 260 nm;

Flow rate: 0.5 ml/min;

Injection volume: 10 µl; and

Column temperature: 40° C.

tinocytes commonly used for evaluating accelerators for differentiating keratinocytes in the skin. Using normal human epidermal keratinocytes (derived from human newborn and commercialized by Kurabo Industries Ltd., Okayama, Japan, and abbreviated as "NHEK cells", hereinafter), the effects of glucosyladenosines on the differentiation of keratinocytes was evaluated by comparing the expression level of profilaggrin, as a marker protein of cells in the granular layer, which is specifically expressed in the cells when keratinocytes differentiate into the cells from those in the basal lamina and which is determined by the western blotting method using an antibody specific to the marker protein. In this experiment, the increment of profilaggrin means that cells in the granular layer have been increased as a result of accelerating the differentiation of keratinocytes in the basal lamina.

TABLE 4

| Composition of permeated solution | Test sample | | | | | |
|---|---|---|---|---|---|---|
| | 5'-Glucosyladenosine | | 3'-Glucosyladenosine | | Adenosine | |
| | Concentration (µM) | Composition (%) | Concentration (µM) | Composition (%) | Concentration (µM) | Composition (%) |
| 5'-Glucosyl-adenosine | 60 | 65 | — | — | — | — |
| 3'-Glucosyl-adenosine | — | — | 25 | 27 | — | — |
| Adenosine | 0 | 0 | 0 | 0 | 0 | 0 |
| Inosine | 1 | 1 | 5 | 5 | 55 | 23 |
| Hypoxanthine | 32 | 34 | 64 | 68 | 187 | 77 |

As evident from Table 4, adenosine was totally metabolized into inosine and hypoxanthine through the step of three-dimensional skin permeation and disappeared. While, 5'- and 3'-glucosyladenosines were partially metabolized into inosine and hypoxanthine but they still remained even after three-dimensional skin permeation at 24 hours after their administrations. The fact indicates that adenosine is promptly metabolized after permeated into the skin and is susceptible to lose its effect, while glucosyladenosine is stably present after permeated into the skin and it reaches the dermis to exert its effect. 5'-Glucosyladenosine was superior to 3'-glucosyladenosine in the stability in three-dimensional skin.

The results in Table 4 revealed that adenosine will disappear because it is relatively promptly hydrolyzed after administered to the skin, while glucosyladenosines are more unsusceptible to hydrolysis in the skin than adenosine. In particular, adenosine is promptly metabolized into inosine and hypoxanthine, but the facts that no adenosine is detected in the case of glucosyladenosines and the formations of inosine and hypoxanthine, as metabolized products of adenosine, are low indicate that the hydrolysis of glucosyladenosines by α-glucosidase gradually proceeds and such glucosyladenosines stay in the skin for a relatively long period of time and sustainably exert their functions.

Experiment 5

Effect of Glucosyladenosines on the Differentiation of Keratinocyte

For the anti-wrinkle action of glucosyladenosines, the effect of glucosyladenosines on keratinocytes in the skin was examined as follows using normal human epidermal kera- <Evaluation Method for the Differentiation of Keratinocytes>

NHEK Cells, which had been suspended in EpiLife medium, commercialized by Caskade Biologics Inc., Oregon, USA, containing EDGS (EpiLife Defined Growth Supplement) (abbreviated as "EpiLife medium containing EDGS", hereinafter), were inoculated to "FALCON MULTI-WELL™ 6WELL", 6-well plate, commercialized by Becton, Dickinson and Co., NJ, USA, which had been coated with "Cellmatorix Type IV", a product name of collagen, commercialized by Nitta Gelatin Inc., Osaka, Japan, in a cell amount of $5×10^5$ cells/1.5 ml/well; and cultured at 37° C. for two days under a 5 v/v % $CO_2$ condition. The culture supernatant in each well was removed by sucking and admixed with a diluent, which had been prepared by adding EpiLife medium to the 5'-glucosyladenosine that had had been prepared in Experiment 1-2 or the 3'-glucosyladenosine that had had been prepared in Experiment 2 to give a final concentration of 0.1 µM, 1 µM or 10 µM, in a volume of 1.5 ml/well. As control 1, adenosine was diluted with EpiLife medium to give a final concentration of 0.1 µM, 1 µM or 10 µM, and the dilution was added to the plates in a volume of 1.5 ml/well. As control 2, EpiLife medium was only added to plates in a volume of 1.5 ml/well. Thereafter, the cells were incubated for eight days while replacing the medium in each well with a fresh preparation of the same medium as added initially every other day. The culture medium in each well was removed by aspiration, and the resulting cells were washed by adding PBS, followed by adding an extraction buffer to the cells in a volume of 100 µl/well, detaching the cells from each well with a cell scraper, and collecting the cells in "EPPENDORF TUBE", a product name of a 1.5 ml microtube, commercialized by Eppendorf AG, Hamburg, Germany. The collected cells were mixed by a vortex mixer, suspended, allowed to stand over ice for 30 min, and centrifuged at 15,000×g for 10 min at 4° C. to collect a supernatant for use as a sample for analysis. 20 mM Tris-HCl buffer (pH 8.0) containing 2% by mass of sodium dodecyl sulfate (SDS), 1 mM edetic acid, 20 µM phenylmethylsulfonyl fluoride (PMSF), 20 µM leupeptin, and 0.1 µM aprotinin was used as an extraction buffer.

<Western Blotting Analysis>

Twelve microliters of the above sample for analysis was added to eight microliters of 2.5 w/v % SDS aqueous solution containing 5 v/v % dithiothreitol (DTT), and the mixture was in usual manner subjected to SDS-polyacrylamide gel electrophoresis after charged on an SDS-polyacrylamide gel in an amount of 20 µg protein per lane. After completing the electrophoresis, proteins contained in the gel were in usual manner transferred to a nitrocellulose membrane, which was then soaked in "BlockAce", a product name of a blocking solution commercialized by Dainippon Sumitomo Pharma Co., Ltd., Osaka, Japan, to inhibit non-specific reactions. The resulting nitrocellulose membrane with the blocking treatment was soaked in a solution, which had been prepared by diluting "Filaggrin (AKH1) Antibody", a product name of an anti-profilaggrin antibody, commercialized by Santa Cruz Biotechnology, Inc., Texas, USA, with 50 mM TBS buffer (50 mM Tris-HCl (pH 7.4) containing 200 mM NaCl) containing 10 v/v % BlockAce (called "TBS buffer", hereinafter) by 100 folds, at ambient temperature for an hour, and washed with 50 mM TBS buffer containing 0.05 v/v % Tween 20 to remove an excessive amount of the antibody. The nitrocellulose membrane was soaked in a solution with an HRP-labeled anti-mouse IgG rabbit polyclonal antibody, commercialized by DAKO, Hamburg, Germany, at ambient temperature for two hours. The resulting nitrocellulose membrane was washed with 50 mM TBS buffer containing 0.05 v/v % Tween 20 for 30 min, and the coloration reaction of the nitrocellulose was carried out using "ECL Western Blotting Detection Reagent and Hyperfilm ECL", a product name of a commercialized western blotting detection kit, commercialized by GE Healthcare UK Ltd., Buckinghamshire, England. As a control, except for using an anti-β-actin antibody in place of the anti-profilaggrin antibody, it was similarly treated as above. The nitrocellulose membrane after coloration was measured for density (strength) of bands with "IMAGE MASTER 1D", a product name of a densitomer, commercialized by Amersham Pharmacia Biotech K.K., Tokyo, Japan, and the band strengths of profilaggrin were divided with the strength of that of β-actin as an internal standard, and the calculated values were used for expression levels. Relative values for the expression levels of profilaggrin in the systems cultured with the addition of 5'-glucosyladenosine, 3'-glucosyladenosine, or adenosine were determined by regarding the expression level of profilaggrin for the control 2 cultured with only EpiLife medium as one, and the results are in Table 5.

TABLE 5

| Test reagent | Concentration in medium (µM) | Expression level of profilaggrin |
| --- | --- | --- |
| With no addition | 0 | 1.0 |
| Adenosine | 0.1 | 1.1 |
|  | 1 | 1.2 |
|  | 10 | 0.9 |
| 5'-Glucosyladenosine | 0.1 | 2.1* |
|  | 1 | 3.8** |
|  | 10 | 2.8** |

TABLE 5-continued

| Test reagent | Concentration in medium (µM) | Expression level of profilaggrin |
| --- | --- | --- |
| 3'-Glucosyladenosine | 0.1 | 1.6* |
|  | 1 | 2.4** |
|  | 10 | 2.0** |

The symbols "*" and "**" mean $P < 0.05$ and $P < 0.01$, respectively, against the production level when the cells were cultured with no addition of test reagent.

As evident from Table 5, when cultured in the medium with the addition of adenosine, no significant enhanced expression level of profilaggrin protein in NHEK cells was observed. While, when cultured in the medium with the addition of 5'-glucosyladenosine or 3'-glucosyladenosine, there were found significant enhanced expression levels of profilaggrin protein as a maker of the cells of the stratum granulosum in the skin. These results indicate that both of the 5'- and 3'-glucosyladenosines have an action of accelerating the differentiation keratinocytes that differentiates keratinocytes of the stratum basale in the skin into cells of the stratum granulosum, and they are preferable as ingredients for external dermal agents with an anti-wrinkle action. Comparing 5'-glucosyladenosine to 3'-glucosyladenosine, the system with the addition of 5'-glucosyladenosine exhibited a stronger enhancing effect on the expression of profilaggrin protein.

Experiment 6

Effect of Glucosyladenosines on Collagen Production

For the anti-wrinkle action of glucosyladenosines, the effect of glucosyladenosines on the collagen production in the dermis was examined as follows using a normal human fetal fibroblast (NHDF) commonly used for evaluating agents for enhancing collagen production in the skin. "NHDF cells", a normal human fetal fibroblast, commercialized by Kurabo Industries Ltd., Okayama, Japan, were suspended in Dulbecco's Minimum Essential Medium (abbreviated as "DMEM", hereinafter) (commercialized by Nissui Pharmaceutical Co., Ltd., Tokyo, Japan) containing 10 v/v % fetal calf serum (abbreviated as "FCS", hereinafter), and the cell suspension was inoculated to "FALCON MULTI-WELL™" 24 WELL, a product name of a 24-well plate, commercialized by Becton, Dickinson and Company, NJ, USA, in a volume of $1.5 \times 10^5$ cells/0.5 ml/well, and incubated at 37° C. for one day under a 5 v/v % $CO_2$ condition. Any one of the 5'-glucosyladenosine prepared in Experiment 1-2, 3'-glucosyladenosine prepared in Experiment 2, and adenosine was diluted with DMEM supplemented with 10 v/v % FCS to give the final concentrations as shown in Table 6, added to the plates in a volume of 0.5 ml/well, and incubated at 37° C. for three days under a 5 v/v % $CO_2$ condition. Thereafter, the culture supernatant in each well was removed by aspiration, and the resulting cells were washed with phosphate buffered saline (PBS), and admixed with pepsin, commercialized by Sigma-Aldrich Co. LLC., Missouri, USA, which had been diluted with 1 M acetic acid to give a concentration of 1 mg/ml, in a volume of 250 µl/well. The resulting plates were shaken at ambient temperature for four hours, and the cells adhered to the wells were detached therefrom with a cell scraper and subjected to pipetting, followed by collecting the resulting cell suspension after the pepsin digestion into "EPPENDORF TUBE", a product name of a 1.5 ml microtube, commercialized by Eppendorf AG, Hamburg, Germany. "Sicrol Collagen Assay Kit", a product name of a developing color reagent for quantifying collagen, commercialized by Biocolor, CA, USA, was added to the tubes in a volume of 500 μl/tube, mixed with a vortex mixer, kneaded by allowing the tubes upside-down at an ambient temperature for exact 30 min using "RT-50", a product name of a rotator commercialized by TAITEC Corporation, Saitama, Japan, and centrifuged (1,500 rpm) at 4° C. for 10 min to remove supernatants. The resulting sediments were admixed with 1 N NaOH in a volume of 100 μl/tube and dissolved by pipetting. The resulting solutions were all transferred to "FALCON MICROTEST™96", a product name of a 96-well microplate commercialized by Becton, Dickinson and Company, NJ, USA, and measured for absorbance (A560-A650) on "Vmax Microplate Reader", a product name of an absorption spectrometer commercialized by Molecular Devices Corporation, CA, USA. The collagen level in each well was determined based on a standard curve prepared by using type I collagen commercialized by KOKEN Co., Ltd., Tokyo, Japan, and the data are shown in Table 6 in parallel.

TABLE 6

| Test reagent | Concentration in medium (μM) | Collagen production level (μg/well) |
|---|---|---|
| With no addition | 0 | 2.53 |
| Adenosine | 5 | 2.61 |
|  | 10 | 3.02* |
| 5'-Glucosyladenosine | 5 | 3.53* |
|  | 10 | 4.54** |
| 3'-Glucosyladenosine | 5 | 3.39* |
|  | 10 | 4.37** |

The symbols "*" and "**" mean P < 0.05 and P < 0.01, respectively, against the collagen production level in a system with no addition of test reagent.

As evident from Table 6, when cultured with the media with the addition of 5 μM adenosine, such culture systems showed no substantial difference compared with the system with no addition of test reagent. While, when NHDF cells were cultured by the addition of 10 μM 5'-glucosyladenosine or 3'-glucosyladenosine, any of such culture systems showed a significantly enhanced collagen production depending on the concentrations of the compounds, where the strengths of the actions of enhancing collagen production by 5'- and 3'-glucosyladenosines were stronger than that of adenosine. The results indicate that 5'- and 3'-glucosyladenosines have superior functions of enhancing collagen production in fibroblasts to adenosine, and they are suitable for ingredients for external dermal agents with an anti-wrinkle action. For reference, the strengths of the actions of augmenting collagen production by 5'- and 3'-glucosyladenosines were approximately equal.

The results in Experiments 5 and 6 show that any of 5'- and 3'-glucosyladenosines have both the action of enhancing the differentiation of keratinocytes in the epidermis and the action of augmenting the collagen production by fibroblasts in the dermis, and they can be used as effective ingredients of external dermal agents having an anti-wrinkle action. The glucosyladenosines were judged to have higher effects than adenosine in terms of the above effects.

Experiment 7

Effect of Glucosyladenosines on the Differentiation of Keratinocytes

Since glucosyladenosines were confirmed in Experiment 5 to have an action of enhancing the differentiation of keratinocytes effective for skin improvement, a test for examining the change of the expression level of a molecular marker gene of keratinocytes, as an index, was performed as follows using a real-time PCR analysis method to examine the above action in more detail. The expression level of a ceramide-synthesis-related gene was also studied to examine the influence of glucosyladenosines on ceramide synthesis that had been known to have an important role in moisturizing the skin and barrier function of the skin and deemed to be effective for skin improvement. As genes for analysis, profilaggrin (PFG: a later differentiation marker) and involucrin (INV: an early differentiation marker) as differentiation markers of keratinocytes and β-glucocerebrosidase (GCase) and sphingomyelinase (SMase) as ceramide-synthesis-related enzymes were selected, and a gene for cyclophilin B (CypB) as an internal standard upon practicing PCR reaction was used (see FIG. 7). NHEK cells were inoculated to 6-well plate coated with collagen in an amount of $8 \times 10^4$ cells/1.5 ml/well, cultured with EpiLife medium, and cultured at 37° C. for two days under a 5 v/v % $CO_2$ condition. Thereafter, the culture medium was removed, and the resulting cells were added with a fresh EpiLife medium containing 5'-glucosyladenosine, 3'-glucosyladenosine, or adenosine in a volume of 1.5 ml/well (giving a final concentration of 1 μM of any one of glucosyladenosines and adenosine), and cultured for seven days while replacing the medium with a fresh one containing any one of glucosyladenosines and adenosine in a volume of 1.5 ml/well every other day. After completion of the culture, each well was washed twice with PBS(K-), followed by adding 0.2 ml/well of 0.025% by mass of trypsin/EDTA solution to the resulting cells and allowing the cells to stand at an ambient temperature for five minutes to detach them from the plates. A neutralizing solution (chelex-treated PBS containing 0.5 v/v % FCS) was added to the plates in a volume of 1 ml/well, followed by collecting the cell suspension in "EPPENDORF TUBE", a product name of a 1.5 ml microtube, commercialized by Eppendorf AG, Hamburg, Germany, while pipetting. The tube was centrifuged at 5,000 rpm for five minutes to remove a supernatant, and the cells separated from the supernatant were subjected to total RNA extraction. As a control, cells cultured with only EpiLife medium were treated similarly as above. Tests were conducted using three wells for each of the control, glucosyladenosines, and adenosine systems.

A commercialized RNA extraction kit, consisting of "QIA SHLEDDER" for cell disruption and "RNeasy Mini Kit", which were product names of GIAGEN Benelux B.V., Netherlands, was used to the total RNA extraction from the above cell pellets, and the handling followed the operating instructions. During the procedure, a treatment with DNase, commercialized by GIAGEN Benelux B.V., Netherlands, was added thereunto. A cDNA template was synthesized by using "M-MLVRT", a product name of a reverse transcriptase commercialized by Gibco, NY., USA, according to the operating instructions as follows: The total RNAs were mixed with an oligo dT random primer, commercialized by Gibco, NY., USA, and "DNA polymerization Mix", a product name of dNTPs, commercialized by GE Healthcare Bioscience, CA, USA, incubated at 70° C. for five minutes, and allowed to stand over ice for at least one minute. To the resultant were added a reverse transcriptase and dithiothreitol, and successively incubated at 25° C. for 10 min, 42° C. for 50 min, and then 70° C. for 15 min.

Nucleotide sequences of primers (forward and reverse primers) requisite for the PCR analysis for an internal standard gene and genes for analysis were either designed from mRNAs available from GENBANK by using "PRIMER 3 SOFTWARE" (a freeware) or prepared with conventionally known nucleotide sequences, and primers were prepared by a contract organization (Sigma-Aldrich Co. LLC., Missouri, USA). The genes for analysis intended by this experiment and the internal standard gene, as well as the nucleotide sequences used as primers for PCR reaction of these genes, are shown in Table 7 in parallel. Using these primers, the expression levels of the genes for analysis were quantified on "LIGHT CYCLER 480", a product name of a commercialized PCR quantification analysis system, produced by Roche Diagnostics K.K., Tokyo, Japan. A PCR reaction for each cDNA template was carried out using "SYBR Green I Master Kit", a product name of a commercialized PCR kit, produced by Roche Diagnostics K.K., Tokyo, Japan; and, based on the operating instructions attached thereunto, a reaction solution was denatured by heating at 95° C. for 5 min and subjected to a PCR reaction (45 cycles of a successive incubation cycle at 95° C. for 10 sec, 60° C. for 10 sec, and 72° C. for 15 sec). Using a DNA encoding cyclophilin B as an internal standard, a relative expression level of each gene for analysis was calculated. Relative expression levels of three wells for each gene for analysis were averaged, when the average of three wells of the expression levels of each gene for analysis in the control was regarded as 1.00, and the data are in Table 8.

TABLE 7

| Gene for analysis and internal standard gene | | Gene sequence | |
| --- | --- | --- | --- |
| Name | Abbreviation | Forward | Reverse |
| Involucrin | INV | SEQ ID NO: 1 | SEQ ID NO: 2 |
| Profilaggrin | PFG | SEQ ID NO: 3 | SEQ ID NO: 4 |
| β-Glucocerebrosidase | GCase | SEQ ID NO: 5 | SEQ ID NO: 6 |
| Sphingomyelinase | SMase | SEQ ID NO: 7 | SEQ ID NO: 8 |
| Cyclophilin B | CypB | SEQ ID NO: 9 | SEQ ID NO: 10 |

TABLE 8

| | Concentration in culture | Gene expression level Gene for Analysis | | | |
| --- | --- | --- | --- | --- | --- |
| Test sample | (μM) | PFG | INV | GCase | SMase |
| With no addition (Contiol) | 0 | 1.00 | 1.00 | 1.00 | 1.00 |
| Adenosine | 1 | 1.41 | 1.15 | 1.37 | 1.35 |
| 3'-Glucosyl-adenosine | 1 | 2.03* | 1.52* | 2.08* | 2.03* |
| 5'-Glucosyl-adenosine | 1 | 2.54** | 1.66** | 2.68** | 2.57** |

The symbols "*" and "**" mean $P < 0.05$ and $P < 0.01$, respectively, against the production level in a system with no addition of test reagent.

As evident from Table 8, NHEK cells showed the expression gene levels of 1.41, 1.15, 1.37 and 1.35 for profilaggrin (PFG), involucrin (INV), β-glucocerebrosidase (GCase), and sphingomyelinase (SMase), respectively, any of the genes showed no significantly enhanced gene expression compared with the gene expression level of the control. On the contrary, when cultured with the addition of 3'-glucosyladenosine, the gene expression levels of 2.03, 1.52, 2.08, and 2.03 for profilaggrin (PFG), involucrin (INV), β-glucocerebrosidase (GCase), and sphingomyelinase (SMase), respectively, all the genes were significantly enhanced compared with the gene expression level of the control. When cultured with the addition of 5'-glucosyladenosine, the gene expression levels of profilaggrin (PFG), involucrin (INV), β-glucocerebrosidase (GCase), and sphingomyelinase (SMase) were respectively increased to 2.54, 1.66, 2.68, and 2.57, which were significantly enhanced compared with the control gene expression level or compared with the system cultured with only medium. These results indicate that the actions of enhancing the differentiation of keratinocytes by 3'- and 5'-glucosyladenosines influence on gene expression levels and the enhancing actions of glucosyladenosines are stronger than that of adenosine even at the genetic level. The fact that the above gene expressions continued for 24 hours or longer after the addition of glucosyladenosines indicates that the effects of glucosyladenosines will continue for at least 24 hours. Comparing 3'-glucosyladenosine to 5'-glucosyladenosine, the above results indicates that the latter's effect is stronger. The results indicate that glucosyladenosines have an important role in synthesizing ceramide, which takes part in an important role in moisturizing the skin and barrier functions of the skin, by acting on β-glucocerebrosidase and sphingomyelinase at their gene levels; and such glucosyladenosines can be also used as expression enhancers for β-glucocerebrosidase and sphingomyelinase, as well as agents for enhancing ceramide synthesis.

Experiment 8

Effect on Keratinocyte Growth Factor

The confirmation that glucosyladenosines have an action of enhancing the differentiation of keratinocytes in Experiments 5 and 7 led to an examination on keratinocyte proliferation. The effects of 5'- and 3'-glucosylkeratinocytes on the expression of keratinocyte growth factor (KGF) in normal human dermal fibroblasts (NHDF) were compared. NHDF Cells were suspended in "Dulbecco's Modified Eagle Medium "Nissui"", a product name of a DMEM medium, commercialized by Nissui Pharmaceutical Co., Ltd., Tokyo, Japan, supplemented with 10% "Fetal Bovine Serum (FBS) Australian Origin", a product name of a serum commercialized by J R Scientific (JRS) Inc., Tokyo, Japan; inoculated to "12-WELL MULTIWELLPLATE", a product name of a 12-well plate, commercialized by Becton, Dickinson and Company, NJ, USA, in an amount of $3\times10^5$ cells/ml/well; and cultured at 37° C. for one day under a 5 v/v % $CO_2$ condition. After the culture, the supernatant in each well was removed and added with 5'-glucosyladenosine obtained by the method in Experiment 1-2 or 3'-glucosyladenosine obtained by the method in Experiment 2, which were respectively diluted with a DMEM medium supplemented with 1 v/v % FCS to give respective concentrations of 0.15 mM and 1.5 mM. A DMEM medium supplemented with 1 v/v % FCS but with no glucosyladenosines was used as a control. The cells were cultured at 37° C. for four hours under a 5 v/v % $CO_2$ condition, washed twice with PBS(−) after removing the culture supernatants in each well by aspiration, and fed to an RNA extraction.

"QIA shledder+RNeasy Mini Kit", a product name of a commercialized RNA extraction kit, produced by GIAGEN Benelux B.V., Netherlands, was used to extract the total RNAs. The handlings followed the operating instructions attached to the kit. Using "Super Script VILO cDNA Synthesis Kit", a product name of a cDNA synthesis kit, commercialized by Invitrogen Corporation, CA, USA, an RT reaction was conducted under the conditions of treating a mixture of 10.5 μl of RNA, three microliters of 5×VILO reaction mix, 1.5 µl of 10× enzyme mix (15 µl in total) at 25° C. for 10 min, 42° C. for 60 min, and then 85° C. for five minutes.

Using "LightCycler 480 SYBR Green I Master", a product name of Roche Diagnostics K.K., Tokyo, Japan, a real-time PCR reaction was conducted by mixing 1.8 µl of water, 6.0 µl of master mix, 0.6 µl of primer L (10 µM), 0.6 µl of primer R (10 µM), and 3.0 µl of template (12.0 µl in total), and treated with 45 cycles of a successive incubation cycle at 95° C. for 10 sec, 60° C. for 10 sec, and 72° C. for 15 sec). The KGF expression level in each sample was calculated from a standard curve and calibrated with the expression level of an internal standard (18s rRNA). Relative value for each sample was determined, when the expression level of the control was regarded as 1.0, and evaluated. The primers used were of Table 9. The results are in Table 10.

TABLE 9

| Objective Gene | Gene sequence | |
|---|---|---|
| | Forward | Reverse |
| KGF | SEQ ID NO: 11 | SEQ ID NO: 12 |
| 18s rRNA | SEQ ID NO: 13 | SEQ ID NO: 14 |

TABLE 10

| Test sample | Concentration (mM) | Relative expression level of KGF |
|---|---|---|
| Control | — | 1.0 |
| 3'-Glucosyladenosine | 0.15 | 2.3 |
| | 1.5 | 2.7 |
| 5'-Glucosyladenosine | 0.15 | 0.9 |
| | 1.5 | 1.4 |

As evident from Table 10, when 3'-glucosyladenosine was used, the KGF expression level increased to 2-folds or higher at a concentration of 0.15 mM or higher. When 5'-glucosyladenosine was used, the KGF expression level increased at a concentration of 1.5 mM or higher. The results indicate that both of 3'- and 5'-glucosyladenosines not only have an action of differentiating keratinocytes but have an action of enhancing their growth, and thus they are preferable as effective ingredients for external dermal agents having an anti-wrinkle action.

The results in Experiments 5, 7 and 8 indicate that since both of 3'- and 5'-glucosyladenosines enhance the differentiation and the growth of keratinocytes, they have an action of improving the turnover of the skin and an advantageous action of inhibiting the generation of wrinkles. The facts that the effects of glucosyladenosines continue even at 24 hours after their additions in Experiment 7 and that these compounds remain in the skin for a relatively long period of time show that the anti-wrinkle actions of glucosyladenosines of the present invention have sustainability. Since 5'-glucosyladenosine had a strong enhancing action on the differentiation of keratinocytes and 3'-glucosyladenosine had a strong enhancing action on the growth of keratinocytes, they can be preferably used in an appropriate combination when used in external dermal agents.

Experiment 9

Cytotoxicity of Glucosyladenosines

To examine whether glucosyladenosines are successively applied to the skin as ingredients for sustainable external dermal agents, they were examined for cytotoxicity. The strengths of cytotoxicity of glucosyladenosines were examined with an index of lactose dehydrogenase (LDH) that is released when cell are damaged, as an influence of glucosyladenosines and adenosine on three dimensional skin. "EPI100 Assay medium", a product name of Kurabo Industries Ltd., Okayama, Japan, was added to "24-WELL MULTIWELL MICROPLATE", a product name of a 24-well plate, commercialized by Becton, Dickinson and Company, NJ, USA, in a volume of 0.19 ml/well; and to each well was transferred "EPI-200 KIT", a product name of a three-dimensional skin model as a skin model cup, commercialized by Kurabo Industries Ltd., Okayama, Japan. The skin model cups were cultured at 37° C. for three hours under a 5 v/v % $CO_2$ condition and transferred to "6-WELL MULTIWELL PLATE", a product name of a 6-well plate, commercialized by Becton, Dickinson and Company, NJ, USA, to which had been added EPI100 assay medium in a volume of 0.9 ml/well. 5'-Glucosyladenosine obtained by the method in Experiment 1-2,3'-glucosyladenosine obtained by the method in Experiment 2, or adenosine was dissolved in 30% ethanol to give respective final concentrations of 5%, and 0.1 ml of any of the resulting solutions was added to each skin model cup, and, after 18 hours, the permeated solution (the medium within each well) was collected. A system, to which 30% ethanol with no glucosyladenosines and adenosine was added, was provided as a control. For the collected media, the activity of lactose dehydrogenase (LDH) released from each skin model was assayed on "CYTOTOXICITY DETECTION KIT (LDH)", a product name of Hoffmann-La Roche Ltd., Basel, Switzerland, and calibrated for obtaining a relative LDH activity by regarding the LDH activity of the control as 1.0 in order to evaluate the cytotoxicity for each sample. The results are in Table 11.

TABLE 11

| Test sample | Concentration (%) | Relative LDH activity |
|---|---|---|
| Control | — | 1.00 |
| 5'-Glucosyladenosine | 5 | 0.79 |
| 3'-Glucosyladenosine | 5 | 0.99 |
| Adenosine | 0.1 | 1.38 |
| | 1 | 3.68 |

As evident from Table 11, when adenosine was used, the LDH activity in the collected solution increased in a concentration-dependent manner, and an apparent LDH release was observed at a concentration of 1%. When 5'- and 3'-glucosyladenosines were used, the LDH activity did not increase even at their respective concentrations of 5% and no LDH release was observed in both cases. The result indicates that adenosine may induce cytotoxicity in a concentration-dependent manner, while the glucosyladenosines of the present invention distinctly hardly induce cytotoxicity on the skin compared with adenosine and that they are useful as effective ingredients for external dermal agents, particularly, effective ingredients for external dermal agents that can be applied to the skin for a relatively long period of time and have a sustainable anti-wrinkle action. As described above, since the glucosyladenosines of the present invention are gradually hydrolyzed by α-glucosidase and the formed adenosine is promptly metabolized, it can be speculated that, even if glucosyladenosines are hydrolyzed into adenosine and glucose by α-glucosidase, such adenosine would not be accumulated as that may cause cytotoxicity.

Experiment 10

Safety of Glucosyladenosines

Glucosyladenosines were evaluated for safety on a patch test with 10 volunteers.
<Subjects>
Twenty male and female (10 males and 10 females), 22 to 45-years-old, were randomly divided into two groups with 10 subjects (five males and five females) each.

<Test Sample>
3'-Glucosyladenosine obtained by the method in Experiment 2 or 5'-glucosyladenosine obtained by the method in Experiment 1-2 was dissolved in refined water to give the following concentrations for use as test samples 1 and 2. Refined water was used as a control.
Test sample 1: An aqueous solution containing 2 w/v % of 3'-glucosyladenosine;
Test sample 2: An aqueous solution containing 2 w/v % of 5'-glucosyladenosine; and
Control: Refined water only.
<Test Method>
A group, consisting of 10 subjects, was applied with test sample 1 and the control (Experiment group 1). Among the 10 subjects, randomly selected five subjects were applied with the control at the inside parts of their left upper arms and applied with test sample 1 at the inside parts of their right upper arms, and the remaining five subjects were applied with the test sample 1 at the inside parts of their left upper arms and applied with the control at the inside parts of their right upper arms. Fifteen microliters of test sample 1 or the control was in usual manner subjected to an occluded application for 24 hours using a finn chamber commercialized by Epitest Ltd., OY, Tuusula, Finland. The remaining one group, consisting of 10 subjects (Experiment group 2), was similarly subjected to a test of occluded application for 24 hours under the same conditions as above except for using 15 µl of test sample 2 in place of test sample 1. At 24 hours after the applications, finn chambers were removed, and the parts with the applications were macroscopically observed at one and 24 hours after removing the chambers. The skin conditions applied with test samples were judged based on the following criteria. The numbers of subjects judged are in Table 12. During the test, the subjects were inhibited to take a bath, shower, or an aggressive movement/activity before removing the finn chambers, do an aggressive movement/activity within 24 hours after removing the chambers, and to take any stimulating action such as a dry skin brushing with a towel, etc., on the parts applied with test samples.

<Evaluation Method>
Based on the Japanese standard from among the criteria for patch tests shown by "Environmental Dermatology" of The Japanese Society For Contact Dermatitis (http://www.daiichiclinic.jp/derma/sesyoku/contents_03/patchtest_table_2.html), the parts with applications were macroscopically judged. The judgments were made based on a scale of six grades: No-reaction (−); slight erythema (±); apparent erythema (+); erythema plus edema, papula, (++); erythema, edema/papula plus blister (+++); and large blister (++++).

TABLE 12

| Experiment group | Applied sample | Time (hour) after removing finn chamber | Macroscopic judgement on parts with sample application (Number of subjects) | | | | | |
|---|---|---|---|---|---|---|---|---|
| | | | − | ± | + | ++ | +++ | ++++ |
| 1 | Test sample 1 | 1 hour | 10 | 0 | 0 | 0 | 0 | 0 |
| | | 24 hours | 10 | 0 | 0 | 0 | 0 | 0 |
| | Control | 1 hour | 10 | 0 | 0 | 0 | 0 | 0 |
| | | 24 hours | 10 | 0 | 0 | 0 | 0 | 0 |
| 2 | Test sample 2 | 1 hour | 10 | 0 | 0 | 0 | 0 | 0 |
| | | 24 hours | 10 | 0 | 0 | 0 | 0 | 0 |
| | Control | 1 hour | 10 | 0 | 0 | 0 | 0 | 0 |
| | | 24 hours | 10 | 0 | 0 | 0 | 0 | 0 |

*: When DMSO was used as a solvent.

As evident from Table 12, no reaction in the parts with applications at 1 and 24 hours after removing the finn chambers was observed in Experiment group 1 applied with test sample 1 (3'-glucosyladenosine) and the control. No reaction in the parts with applications at 1 and 24 hours after removing the finn chambers was observed in Experiment group 2 applied with test sample 2 (5'-glucosyladenosine) and the control. These results indicate that glucosyladenosines are safe substances even when applied to the skin.

The present invention is concretely explained with reference to the following Examples but they should never restrict the scope of the present invention.

Example 1

Particulate Composition Containing Glucosyladenosines

Adenosine, a special grade reagent of Wako Pure Chemical Industries, Ltd., Tokyo, Japan, and "PINEDEX #1", a product name of a dextrin with a solid content of about 92.3% by mass, commercialized by Matsutani Chemical Industry Co., Ltd, Hyogo, Japan, were respectively added to 6,600 ml of 2 mM $CaCl_2$ solution to give final concentrations of 1 w/v % and 10 w/v %, respectively, and the solution was heated to 50° C. and completely dissolved by stirring. The resulting solution was adjusted to pH 6.0 with 1N HCl, admixed with 30 ml of an enzyme solution prepared by diluting a concentrated crude enzyme solution, which had been prepared by culturing *Bacillus circulans* PP710 strain, deposited with International Patent Organism Depositary in National Institute of Advanced Industrial Science and Technology, Tsukuba Central 6, 1-1, Higashi 1-chome, Tsukuba-shi, Ibaraki-ken, 305-8566 Japan, under the accession number of FERM BP-10771, which had had been prepared in Experiment 1-1, with 50 mM acetate buffer (pH 6.0) to give an α-glucosyltransferase solution with an activity of 500 units/ml, in an amount of 20 units/g dextrin of α-glucosyltransferase, mixed by stirring, and enzymatically reacted at 50° C. for 24 hours. After completion of the enzymatic reaction, 1N HCl was added to the resulting enzymatic reaction solution to give a pH of 3.5, admixed with "XL-4", a product name of a glucoamylase, 3,800 units/ml, commercialized by Nagase Biochemicals, Ltd., Osaka, Japan, in an amount of 1,000 units/g dextrin at 50° C. for 24 hours, and heated at 100° C. for 10 min to suspend the enzymatic reaction. The resulting enzymatic reaction solution was fed to an activated charcoal column, 100 mm×ø41 mm, at an SV=3 (5 ml/min), to adsorb glucosyladenosines to the column, followed by washing the column with deionized water in a volume of 5-folds of the wet charcoal volume and 20 v/v % ethanol solution in a volume of 3-folds of the wet charcoal volume and eluting the adsorbed ingredients with 40 v/v % ethanol solution. The eluate was fractionated by 50 ml, followed by collecting fractions with an ultraviolet absorption (260 nm) of 0.15 or higher. The collected fractions were pooled, concentrated with a rotary evaporator, fed to a column consisting of two columns of "XT-1030E" (Na-form), 04.2 cm×100 cm, a product name of a strongly-acidic cation exchange resin, commercialized by Organo Corporation, Tokyo, Japan, at a flow rate of 40 ml/min, and eluted with deionized water. The collected fractions were analyzed on HPLC under the same conditions as in Experiment 3, followed by collecting fractions that had been calculated to contain at least 95% by mass of glucosyladenosines. These fractions were pooled and dried in vacuo to obtain 15 g of a powder containing glucosyladenosines. The product contained, on a dry solid basis, about 85% by mass of 5'-glucosyladenosine, about 10% by mass of 3'-glucosyladenosine, about 0.3% by mass of nigerosyl adenosine, and about 2% by mass of adenosine. The product can be used intact or after either admixed with appropriate carriers, fillers/excipients/adjuvants, stabilizers, buffers, pH-regulators, media, and arbitral auxiliary agents, or made into compositions in the form of a pharmaceutical, quasi-drug, or cosmetic as an effective ingredient for external dermal agents having a sustainable anti-wrinkle action to assist the maintenance and improvement of systemic structure and physiological functions in the epidermis and the dermis. Also the product can be arbitrarily used as an agent for differentiating and proliferating the growth of keratinocytes, augmenting the production of collagen, and accelerating the synthesis of ceramide, as well as being used a humectant.

For reference, the above nigerosyl adenosine was observed as a minor peak with a retention time of about 22 to 23 min between the elution peak of adenosine and that of 3'-glucosyladenosine other than the elution peaks of 5'- and 3'-glucosyladenosines and adenosine. When the fraction corresponding to such a minor peak was collected and subjected to mass spectrum (MS) analysis in usual manner, it was calculated to have a molecular weight of 607 and judged to be a compound composed of two molecules of glucose bound to adenosine. Using the collected fraction and based on the chemical shift (see Table 13) of the carbons and protons of the fraction on MNR analysis under the following conditions, the substance contained in the fraction was identified as 5'-nigerosyladenosine (α-D-glucopyranosyl-(1→3)-α-D-glucopyranosyl-(1→5')-adenosine; 5'-α-nigerosyladenosine). Since 5'-nigerosyladenosine dissolves in deuterium water in an amount of at least 6 w/v %, it has a higher solubility in aqueous media than 3'-glucosyladenosine. The carbon chemical shifts of adenosine and nigerose were obtained from the spectrum data base of organic compounds opened by The National Institute of Advanced Industrial Science and Technology (AIST) (SDBS; http://riodb01.ibase.aist.go.jp/sdbs/cgi-bin/direct_frame_top.cgi).

<HPLC Conditions>

Apparatus: SHIMADZU UV-VIS DETECTOR SPD-20A (a detector), LC-20AB (a pump), C-R7Aplus (a recorder), SIL-20AC (an autosampler);

Column: "YMC-PACK ODS-AQ303", ø4.6 mm×250 mm, a product name of an ODS column commercialized by YMC Co., Ltd., Kyoto, Japan;

Mobile phase: {20 mM ammonium acetate buffer (pH 3.5)}/(methanol)=92/8 (v/v);

Detection wavelength: 260 nm;

Flow rate: 0.5 ml/min;

Injection volume: 20 μl;

Column temperature: 40° C.;

<NMR Analysis Conditions>

Apparatus: "JNM-AL300", $^1$H: 300.4 MHz, $^{13}$C: 75.45 MHz, a product name of JJEOL Ltd., Tokyo, Japan;

Medium: Deuterium water (0.6 ml);

Internal standard: Sodium 3-(trimethylsilyl)-1-propanesulfonate (TPS);

Number of scans: Sixty-four times for $^1$H-NMR; 1,200 times for $^{13}$C-NMR; 100 times for DEPT; 36 times for H—H COSY; 72 times for H—C COSY; and 920 times for HMBC;

Sample amount: 36.4 mg.

|  |  | Carbon number | Adenosine* | Nigerose* | δc (ppm) Glucosyl-adenosine prepared in Experiment 1-2 | Glucosyl-adenosine prepared in Experiment 2 | Minor peak of the product | δH (ppm) Minor peak of the product | |
|---|---|---|---|---|---|---|---|---|---|
| Adenosine | Adenine | 1 | 155.5 | — | 157.2 | 157.6 | 152.4 | — | — |
|  |  | 2 | 152.1 | — | 154.6 | 154.5 | 147.2 | 8.31 | (s, 1H) |
|  |  | 3 | 149.0 | — | 150.6 | 150.7 | 150.9 | — | — |
|  |  | 4 | 141.4 | — | 142.4 | 142.9 | 145.4 | 8.68 | (s, 1H) |
|  |  | 5 | 119.6 | — | 120.5 | 121.3 | 121.0 | — | — |
|  | Ribose | 1' | 88.9 | — | 89.7 | 90.6 | 90.4 | 6.05 | (d, 1H) |
|  |  | 2' | 74.3 | — | 76.6 | 75.6 | 86.3 | 4.30 | (m, 1H) |
|  |  | 3' | 71.1 | — | 71.8 | 79.1 | 77.3 | 4.59 | (t, 1H) |
|  |  | 4' | 86.3 | — | 85.4 | 86.6 | 73.0 | 4.36 | (t, 1H) |
|  |  | 5' | 62.0 | — | 69.0 | 63.7 | 69.2 | 3.63 & 3.98 | (dd, 1H) |

-continued

| | | | | δc (ppm) | | | | δH (ppm) | |
|---|---|---|---|---|---|---|---|---|---|
| | | Carbon number | Adenosine* | Nigerose* | Glucosyl-adenosine prepared in Experiment 1-2 | Glucosyl-adenosine prepared in Experiment 2 | Minor peak of the product | | Minor peak of the product |
| Nigerose | Glucose | 1″ | — | 93.4 | 100.7 | 101.8 | 100.9 | 4.86 | (d, 1H, $J_{1,2}$ = 3.49) |
| | | 2″ | — | 71.2 | 73.6 | 73.9 | 72.3 | 3.56 | (t, 1H) |
| | | 3″ | — | 80.9 | 75.5 | 75.1 | 81.7 | 3.68 | (t, 1H) |
| | | 4″ | — | 70.5 | 71.8 | 71.9 | 72.3 | 3.27 | (t, 1H) |
| | | 5″ | — | 72.4 | 74.5 | 75.1 | 74.4 | 3.46 | (m, 1H) |
| | | 6″ | — | 61.4 | 62.8 | 62.9 | 62.8 | 3.42 & 3.49 | (dd, 2H) |
| | Glucose | 1‴ | — | 100.2 | — | — | 101.2 | 5.24 | (d, 1H, $J_{1,2}$ = 3.67) |
| | | 2‴ | — | 72.9 | — | — | 74.1 | 3.38 | (t, 1H) |
| | | 3‴ | — | 74 | — | — | 75.2 | 3.60 | (t, 1H) |
| | | 4‴ | — | 71.2 | — | — | 71.9 | 3.27 | (t, 1H) |
| | | 5‴ | — | 72.9 | — | — | 74.2 | 3.86 | (m, 1H) |
| | | 6‴ | — | 61.6 | — | — | 62.8 | 3.42 & 3.49 | (dd, 2H) |

Example 2

Two and half grams of glucosyladenosine prepared in Example 1 was dissolved by the addition of 100 ml of refined water, and the solution was fed to a preparative HPLC using an ODS column under the same conditions as in Experiment 1-2, followed by collecting a fraction containing 5′-glucosyladenosine and dried in vacuo to prepare a particulate composition containing at least 99% by mass of 5′-glucosyladenosine, d.s.b., in a total amount of about 1.6 g. The product can be used intact or after admixed with appropriate carriers, fillers/excipients/adjuvants, stabilizers, buffers, pH-regulators, media, and arbitral auxiliary agents, as an effective ingredient for external dermal agents having a sustainable anti-wrinkle action to assist the maintenance and improvement of systemic structure and physiological functions in the epidermis and the dermis. Also the product can be arbitrarily used as an agent for enhancing the differentiation and the proliferation of keratinocytes, augmenting the production of collagen, and accelerating the synthesis of ceramide, as well as being used a humectant.

Example 3

Particulate Composition Containing Glucosyladenosines

Adenosine, a special grade reagent of Tokyo Chemical Industry Co., Ltd., (TCI), Tokyo, Japan, and "PINEDEX #1", a product name of a dextrin with a solid content of about 92.3% by mass, commercialize by Matsutani Chemical Industry Co., Ltd, Hyogo, Japan, were respectively added to 10 mM sodium acetate solution (pH 5.5) to give respective concentrations of 1 w/v % and 10 w/v %, and the solution was heated to 50° C. and completely dissolved by stirring. To the resulting solution was added a CGTase derived from *Geobacillus stearothermophilus* Tc-91 strain, deposited with International Patent Organism Depositary in National Institute of Advanced Industrial Science and Technology, Tsukuba Central 6, 1-1, Higashi 1-chome, Tsukuba-shi, Ibaraki-ken, 305-8566 Japan, under the accession number of FERM BP-11273, in an amount of 1,000 units/g dextrin, and subjected to an enzymatic reaction at 50° C. for 24 hours. After completion of the enzymatic reaction, the resulting enzymatic reaction solution was heated at 100° C. for 15 min to inactivate the remaining CGTase, admixed with "GLUCOZYME #20000", a product name of a glucoamylase, 20,000 units/g, commercialized by Nagase ChemteX Corporation, Osaka, Japan, in an amount of 2,600 units/g dextrin, and subjected to an enzymatic reaction at 50° C. for 24 hours. The resulting enzymatic reaction solution was heated at 100° C. for 10 min and centrifuged at 11,500 rpm to collect a supernatant in a volume of 800 ml. The supernatant was passed through a column, 120 mm×ø41 mm, packed with 150 ml of an activated charcoal at an SV=3 (5 ml/min) to adsorb glucosyladenosines and adenosine on the column, followed by washing the column with deionized water in an amount of seven-folds volume of the wet charcoal volume and 20 v/v % ethanol solution in an amount of six-folds of the wet charcoal volume, and eluting the adsorbed ingredients with 40 v/v % ethanol solution in an amount of 16-folds of the wet charcoal volume. The eluate was fractionated by 50 ml, followed by collecting fractions observed with an ultraviolet absorption (260 nm). About a half volume of the collected fractions was filtered with a membrane having a pore size of 0.22 μm and dried in vacuo to obtain about four grams of a particulate composition containing glucosyladenosines. The product contained, on a dry solid basis, about 26% by mass of 5′-glucosyladenosine, about 52% by mass of 3′-glucosyladenosine, and about 21% by mass of adenosine. The product can be used intact or after admixed with appropriate carriers, fillers/excipients/adjuvants, stabilizers, buffers, pH-regulators, media, and arbitral auxiliary agents, as an effective ingredient for external dermal agents having a sustainable anti-wrinkle action to assist the maintenance and improvement of systemic structure and physiological functions in the epidermis and the dermis. Also the product can be arbitrarily used as an agent for enhancing the differentiation and the proliferation of keratinocytes, augmenting the production of collagen, and accelerating the synthesis of ceramide, as well as being used a humectant.

Example 4

The remaining half amount of the fractions, which had been collected in Example 3 as an eluent from the activated charcoal column, was subjected to a preparative HPLC using an ODS column under the same conditions as in Experiment 1-2, followed by collecting 3′- and 5′-glucosyoadenosine fractions respectively and desalting the fractions with a column chromatography using a column packed with an activated charcoal similarly as in Example 3, and eluting the adsorbed ingredients with 40 v/v % ethanol solution to collect fractions with glucosyladenosines. The collected fractions were pooled, filtered with a membrane having a pore size of 0.22 μm, and dried in vacuo to obtain about 1.6 g of a specimen containing at least 99% by mass of 3'-glucosyladenosine and about 0.6 g of a specimen containing at least 99% by mass of 5'-glucosyladenosine. The products can be used intact or after added with appropriate carriers, fillers/excipients/adjuvants, stabilizers, buffers, pH-regulators, media, and arbitral auxiliary agents, as effective ingredients for external dermal agents having a sustainable anti-wrinkle action to assist the maintenance and improvement of systemic structure and physiological functions in the epidermis and the dermis. Also the product can be arbitrarily used as an agent for enhancing the differentiation and the proliferation of keratinocytes, enhancing the production of collagen, and accelerating the synthesis of ceramide, as well as being used a humectant.

Example 5

Particulate Composition Containing Glucosyladenosines

Adenosine, a special grade reagent of Tokyo Chemical Industry Co., Ltd., (TCI), Tokyo, Japan, and "PINEDEX #1", a product name of a dextrin with a solid content of about 92.3% by mass, commercialized by Matsutani Chemical Industry Co., Ltd, Hyogo, Japan, were respectively added to 10 mM sodium acetate solution (pH 5.5) to give respective concentrations of 1 w/v % and 10 w/v %, and the solution was heated to 50° C. and completely dissolved by stirring. To the resulting solution was added a CGTase derived from *Geobacillus stearothermophilus* Tc-91 strain, deposited with International Patent Organism Depositary (IPOD) National Institute of Technology and Evaluation (NITE) (former International Patent Organism Depositary, National Institute of Advanced Industrial Science and Technology), Tsukuba Central 6, 1-1, Higashi 1-chome, Tsukubashi, Ibaraki-ken, 305-8566 Japan, under the accession number of FERM BP-11273, in an amount of 1,000 units/g dextrin, and subjected to an enzymatic reaction at 50° C. for 24 hours. After completion of the enzymatic reaction, the resulting enzymatic reaction solution was heated at 100° C. for 15 min to inactivate the remaining CGTase, and centrifuged at 11,500 rpm to collect 400 ml supernatant. The supernatant was passed through a column, 120 mm×ø41 mm, packed with 150 ml of an activated charcoal, at an SV=3 (5 ml/min) to adsorb glucosyladenosines including glucosyladenosines and adenosine on the column, followed by washing the column with deionized water in 7-folds volume of the wet charcoal volume and 20 v/v % ethanol solution in 6-folds of the wet charcoal volume, and eluting the adsorbed ingredients with 40 v/v % ethanol solution in 16-folds volume of the wet charcoal volume. The eluate was fractionated by 50 ml, followed by collecting fractions with an ultraviolet absorption (260 nm). The collected fractions were pooled and filtered with a membrane having a pore size of 0.22 μm and dried in vacuo to obtain about five grams of a particulate composition containing adenosine and glycosyladenosines including glucosyladenosines. The product contained, on a dry solid basis, 3'-glycosyladenosines such as 3'-glucosyladenosine, 3'-maltosyladenosine, and 3'-maltotoriosyladenosine, and 5'-glycosyladenosines such as 5'-glucosyladenosine, 5'-maltosyladenosine, and 5'-maltotoriosyladenosine in a total amount of about 58% by mass; and adenosine in a total amount of about 37% by mass. About 30% by mass of the glycosyladenosines in the product had been glycosylated at the C-5' position of adenosine. The product can be used intact or after admixed with appropriate carriers, fillers/excipients/adjuvants, stabilizers, buffers, pH-regulators, media, and arbitral auxiliary agents, as an effective ingredient for external dermal agents having a sustainable anti-wrinkle action to assist the maintenance and improvement of systemic structure and physiological functions in the epidermis and the dermis. Also the product can be arbitrarily used as an agent for enhancing the differentiation and the proliferation of keratinocytes, enhancing the production of collagen, and accelerating the synthesis of ceramide, as well as being used a humectant.

Example 6

Composition Containing Glucosyladenosines

To one part by weight of any one of the particulate compositions containing glucosyladenosines prepared by the method in Examples 1 to 5 was added two parts by weight of α,α-trehalose, and the mixture was mixed to homogeneity to prepare a composition containing glucosyladenosines. The product can be used as an effective ingredient for external dermal agents having a sustainable anti-wrinkle action to assist the maintenance and improvement of systemic structure and physiological functions in the epidermis and the dermis. Also the product can be arbitrarily used as an agent for enhancing the differentiation and the proliferation of keratinocytes, enhancing the production of collagen, and accelerating the synthesis of ceramide, as well as being used a humectant.

Example 7

Composition Containing Glucosyladenosines

To two parts by weight of any one of particulate compositions containing glucosyladenosines prepared by the method in Examples 1 to 5 was added three parts by weight of a particulate composition (prepared at Hayashibara Biochemical Laboratories Inc., Okayama, Japan), which had been obtained by spray drying "TORNALE", commercialized by Hayashibara Co., Ltd., Okayama, Japan, and the mixture was mixed to homogeneity to prepare a composition containing glucosyladenosines. The product can be used as an effective ingredient for external dermal agents having a sustainable anti-wrinkle action to assist the maintenance and improvement of systemic structure and physiological functions in the epidermis and the dermis. Also the product can be arbitrarily used as an agent for enhancing the differentiation and the proliferation of keratinocytes, enhancing the production of collagen, and accelerating the synthesis of ceramide, as well as being used a humectant.

Example 8

Composition Containing Glucosyladenosines

To any one of particulate compositions containing glucosyladenosines prepared by the methods in Examples 1 to 5 were added five parts by weight of "AA2G™", a product name of ascorbic acid 2-glucoside commercialized by Hayashibara Biochemical Laboratories Inc., Okayama, Japan, and 0.1 part by weight of edetate disodium, and the mixture was mixed to homogeneity to obtain a composition containing glucosyladenosines. The product can be used as an effective ingredient for external dermal agents having a sustainable anti-wrinkle action to assist the maintenance and improvement of systemic structure and physiological functions in the epidermis and the dermis. Also the product can be arbitrarily used as an agent for enhancing the differentiation and the proliferation of keratinocytes, enhancing the production of collagen, and accelerating the synthesis of ceramide, as well as being used a humectant.

Example 9

Composition Containing Glucosyladenosines

To 20 parts by weight of refined water were added one part by weight of any one of particulate compositions containing glucosyladenosines prepared by the methods in Examples 1 to 5, two parts by weight of α-glucosylhesperidin or α-glucosylrutin, and one part by weight of cyclonigerosylnigerose (a cyclictetra saccharide produced by Hayashibara Biochemical Laboratories Inc., Okayama, Japan), and the mixture was dissolved by stirring, and spray dried in usual manner to prepare a composition containing glucosyladenosines. The product can be used as an effective ingredient for external dermal agents having a sustainable anti-wrinkle action to assist the maintenance and improvement of systemic structure and physiological functions in the epidermis and the dermis. Also the product can be arbitrarily used as an agent for enhancing the differentiation and the proliferation of keratinocytes, enhancing the production of collagen, and accelerating the synthesis of ceramide, as well as being used a humectant.

<Example of Composition 1: External Dermal Agent in the Form of a Cream>

| Composition ingredient | (% by mass) |
| --- | --- |
| (1) Propylene glycol | 5 |
| (2) Beeswax | 5 |
| (3) Cetyl alcohol | 4 |
| (4) Lanolin, hydrogenated | 5 |
| (5) Squalane | 35 |
| (6) Stearyl glyceride | 2 |
| (7) Polyoxyethylene (20 moles) sorbitan monolaurate | 2 |
| (8) 3'- or 5'-Glucosyladenosine prepared in Example 4 | 1 |
| (9) Antiseptic | q.s. |
| (10) Flavor | q.s. |

Volume up the total volume to 100% by mass with refined water.

<Anti-Wrinkle Action of External Dermal Agent Incorporated with Glucosyladenosine>

To confirm the effectiveness of the external dermal agent of the present invention, a test with volunteers was conducted using a cream with the above example of composition 1 incorporated with 3'- or 5'-glucosyle adenosine as an effective ingredient. Forty females, 30- to 50-years-old, were selected as volunteers suffering from chronic rough skin on a questionnaire and randomly grouped into four groups, 10 volunteers each. Ten volunteers in one group were allowed to apply the above cream (cream 1 incorporated with 3'-glucosyladenosine) at a part with rough skin three times a day (morning, noon, and evening) for one month every day. The volunteers of another one group were allowed to apply the above cream (cream 2 incorporated with 5'-glucosyladenosine) at a part with rough skin three times a day (morning, noon, and evening) for one month every day. Ten volunteers of the other group were allowed to apply a cream with the same composition as the above creams (cream 3 incorporated with 1% by mass of adenosine in place of any of the glucosyladenosines in the above creams) at a part with rough skin three times a day (morning, noon, and evening) for one month every day. Ten volunteers of the remaining group were allowed to apply a cream (cream 4) with the same composition as in the above creams except for neither containing glucosyladenosines nor adenosine at a part with rough skin three times a day (morning, noon, and evening) for one month every day. Moisture content in the skin was measured on the following method and the conditions of wrinkles were evaluated as wrinkle scores for judging the conditions of rough skin. In this method, the higher the moisture content in the skin after applying a test sample becomes compared with the level before the application and the lower the wrinkle score becomes, the more the rough skin is improved.

<Method for Assaying Moisture Content in the Skin>

On the previous and the next day of applying a cream, the moisture content and the wrinkle score in the skin applied with any one of the creams were determined. For assaying the moisture content in the skin, "SKICON-200EX", a product name of an apparatus for measuring moisture content, commercialized by IBS Co., Ltd., Shizuoka, Japan, and the moisture contents of 10 volunteers applied with each cream were averaged and shown in Table 15.

<Method for Judging Wrinkle Score>

For judging wrinkle scores, every volunteers were macroscopically evaluated by five judges based on the guideline for the evaluation of the efficacy of cosmetic products (see, "*Journal of Japanese Cosmetic Science Society*", Vol. 30, No. 4, pp. 316-332, 2006) using the eight grades of wrinkle scores (grades 0 to 7) in Table 14. The judgments by the five judges for each volunteer were averaged for the volunteer's wrinkle score and the average of 10 volunteers applied with any one of the creams is in Table 15.

TABLE 14

| Wrinkle score (Grade) | Criteria of judgement |
| --- | --- |
| 0 | No wrinkle |
| 1 | Unclear, shallow wrinkle is slightly observed |
| 2 | Clear, shallow wrinkle is slightly observed |
| 3 | Clear, shallow wrinkle is observed |
| 4 | Rather deep wrinkle is slightly observed in clear shallow wrinkle |
| 5 | Rather deep wrinkle is observed |
| 6 | Clear deep wrinkle is observed |
| 7 | Distinctly deep wrinkle is observed |

TABLE 15

| Test cream | | Moisture content in the skin (µS) | Wrinkle score |
| --- | --- | --- | --- |
| Cream 1 | Before application | 18 ± 4 | 2.08 |
|  | After application | 28 ± 3* | 1.22* |

TABLE 15-continued

| Test cream | | Moisture content in the skin (µS) | Wrinkle score |
|---|---|---|---|
| Cream 2 | Before application | 17 ± 2 | 2.12 |
|  | After application | 24 ± 2* | 1.42* |
| Cream 3 | Before application | 17 ± 5 | 2.12 |
|  | After application | 21 ± 6 | 1.88 |
| Cream 4 | Before application | 17 ± 3 | 2.18 |
|  | After application | 19 ± 2 | 2.02 |

The symbol "*" means "$P < 0.05$" compared with that before the application of each cream.

As evident from Table 15, in the case of applying a cream (cream 1 or 2) incorporated with any of glucosyladenosines, the moisture content in the skin and the wrinkle score after application were significantly improved and the rough skin was improved compared with those before application. On the contrary, when applied with a cream (cream 3) incorporated with adenosine in place of glucosyladenosines and a cream (cream 4) incorporated with neither glucosyladenosines nor adenosine, the moisture content in the skin and the wrinkle score even after application were not significantly improved and the rough skin was not improved compared with those before administration. Comparing between the creams incorporated with glucosyladenosines, the volunteers applied with a cream (cream 2) incorporated with 5'-glucosyladenosine tended to show a higher improvement effect on the moisture content in the skin and the wrinkle score compared to those applied with a cream (cream 1) incorporated with 3'-glucosyladenosine, resulting in a judgement that 5'-glucosyladenosine has a higher rough skin improving effect than 3'-glucosyladenosine. Since no abnormality inherent to the application of the cream (cream 1 or 2) incorporated with any of glucosyladenosines was induced during and after completion of the test, it was judged that glucosyladenosines have an advantageous safeness.

<Example of Composition 2: Composition in the Form of a Liquid>

| Composition ingredient | (% by mass) |
|---|---|
| (1) Glycerin | 3 |
| (2) Propylene glycol | 4 |
| (3) Ethanol | 8 |
| (4) Polyoxyethylene(20 moles) olein alcohol | 0.5 |
| (5) Any one of particulate compositions containing glucosyladenosines prepared by the methods in Examples 1 to 5 or any one of compositions containing glucosyladenosines prepared by the methods in Examples 6 to 8 | 0.5<br>3 |
| (6) *Magnolia denudata* extract | 2 |
| (7) Citric acid | 0.01 |
| (8) Sodium citrate | 0.1 |
| (9) 1,2-Pentane diol | 0.1 |
| (10) Flavor | 0.05 |

Volume up the total volume to 100% by mass with refined water.

<Example of Composition 3: External Dermal Agent in the Form of a Pack>

| Composition ingredient | (% by mass) |
|---|---|
| (1) Polyvinyl alcohol | 15 |
| (2) Polyethylene glycol | 3 |
| (3) Propylene glycol | 7 |
| (4) Ethanol | 10 |
| (5) *Tricholoma matsutake* extract | 1 |
| (6) Any one of particulate compositions containing glucosyladenosines prepared by the methods in Examples 1 to 5 or any one of compositions containing glucosyladenosines prepared by the methods in Examples 6 to 8 | 0.1<br>0.5 |
| (7) 1,2-Pentane diol | 0.1 |
| (8) Flavor | q.s. |

Volume up the total volume to 100% by mass with refined water.

<Example of Composition 4: Chapstick>

A chapstick was prepared with the following composition in usual manner.

| Composition ingredient | (% by mass) |
|---|---|
| (1) Dextrin fatty acid ester | 8.0 |
| (2) Beeswax | 4.0 |
| (3) Microcrystalline wax | 3.0 |
| (4) Caprylic triglyceride | 15.0 |
| (5) Diglyceryl triisostearate | 20.0 |
| (6) Diisostearyl malate | 32.0 |
| (7) Polybutene | 10.0 |
| (8) Tocopherol acetate | 2.0 |
| (9) 5'-Glucosyladenosine prepared by the method in Example 2 | 2.0 |
| (10) *Glycyrrhiza* extract | 0.1 |
| (11) 1,2-Pentane diol | 0.1 |
| (12) Flavor | q.s. |

<Example of Composition 5: External Dermal Agent in the Form of a Gel>

| Composition ingredient | (% by mass) |
|---|---|
| (1) Trioctanoyl rain | 51.3 |
| (2) "HALLODEX", a product name of a syrup containing saccharide derivatives of α,α-trehalose | 16.4 |
| (3) Polyglyceryl(10) monomyristate | 5.2 |
| (4) Polyglyceryl(10) monostearate | 1.75 |
| (5) Ascorbic acid 2-glucoside | 1 |
| (6) *Glycyrrhiza* extract | 0.1 |
| (7) Hyaluronic acid | 0.25 |
| (8) Any one of particulate compositions containing glucosyladenosines prepared by the methods in Examples 1 to 5 or any one of compositions containing glucosyladenosines prepared by the methods in Examples 6 to 8 | 0.2<br>1.0 |
| (9) 1,2-Pentane diol | 0.1 |
| (10) Flavor | q.s. |

Volume up the total volume to 100% by mass with refined water.

<Examples of Composition 6: External Dermal Agent in the Form of an Ointment>

| Composition ingredient | (% by mass) |
|---|---|
| (1) Sodium acetate | 1.0 |
| (2) Calcium hydrogen phosphate | 4.0 |
| (3) Glycerin | 10.0 |
| (4) Mint oil | 0.5 |
| (5) Green tea extract | 0.6 |
| (6) L-Ascorbic acid 2-glucoside | 2.0 |
| (7) 1,2-Hexane diol | 0.1 |
| (7) Petrolatum | 49.0 |
| (8) Japanese wax | 10.0 |
| (9) Lanolin | 10.0 |
| (10) Sesame oil | 10.5 |

The external dermal agents with these examples of compositions sustainably exert an anti-wrinkle action when used in their typical forms and improve conditions in the skin.

INDUSTRIAL APPLICABILITY

As described above, the external dermal agent containing α-D-glucopyranosyl-(1→3')-adenosine and/or α-D-glucopyranosyl-(1→5')-adenosine of the present invention has both the action of enhancing the proliferation and the differentiation of keratinocytes in the skin and the action of augmenting the collagen production of fibroblasts in the dermis. Since the agent stably exerts the above actions in the skin, it can be used in industries for producing cosmetics, pharmaceuticals, quasi-drugs, miscellaneous goods, etc., as an external dermal agent having an outstanding sustainable anti-wrinkle action to assist the maintenance and improvement of tissue structures and physiological functions of the epidermis and the dermis. The present invention is a significant invention that has such remarkable effects and functions and greatly contributes to the art.

| | | |
|---|---|---|
| 0-1 | Form PCT/RO/134 (SAFE) | JPO-PAS |
| 0-1-1 | Indications (PCT Rule 13-2) relating to deposited microorganisms and other biological materials were drafted by means as indicated in the right column | i180 |
| 0-2 | International Patent Application Number | |
| 0-3 | Document code for applicant or patent attorney | WO1239 |
| 1 | The following indications relate to microorganisms or biological materials disclosed in the detailed description of the invention | 0062 |
| 1-1 | Paragraph number | |
| 1-3 | Depositary indication | International Patent Organism Depositary (IPOD) National Institute of Technology and Evaluation (NITE) Tsukuba Central 6, 1-1, Higashi 1-chome, Tsukuba-shi, Ibaraki-ken, 305-8566 Japan Feb. 1, 2007 (01.02.2007) IPOD FERM BP-10771 |
| 1-3-1 | Name of depository | |
| 1-3-2 | Address | |
| 1-3-3 | Date of deposition | |
| 1-3-4 | Deposit number | |
| 1-5 | Designated countries for representing the indications | All the designated countries |
| 2 | The following indications relate to microorganisms or biological materials disclosed in the detailed description of the invention | 0066 |
| 2-1 | Paragraph number | |
| 2-3 | Depositary indication | International Patent Organism Depositary (IPOD) National Institute of Technology and Evaluation (NITE) Tsukuba Central 6, 1-1, Higashi 1-chome, Tsukuba-shi, Ibaraki-ken, 305-8566 Japan Jul. 30, 1973 (30.07.1973) IPOD FERM BP-11273 |
| 2-3-1 | Name of depository | |
| 2-3-2 | Address | |
| 2-3-3 | Date of deposition | |
| 2-3-4 | Deposit number | |
| 2-5 | Designated countries for representing the indications | All the designated countries |
| | | Column to be filled in by a receiving office |
| 0-4 | This sheet was received along with the international application (yes/no) | |
| 0-4-1 | Authorized personnel | |
| | | Column to be filled in by the International Bureau |
| 0-5 | Date of this sheet received | |
| 0-5-1 | Authorized personnel | |

The invention claimed is:

1. A method for treating the skin so as to avoid wrinkling, comprising applying an external dermal agent having a sustainable anti-wrinkle action to the skin, said external dermal agent comprising α-D-glucopyranosyl-(1→5')-adenosine and/or α-D-glucopyranosyl-(1→3')-adenosine as an effective ingredient(s) and a carrier selected from the group consisting of cosmetically and pharmaceutically acceptable carriers.

2. The method of claim 1, wherein said external dermal agent comprises a further ingredient selected from the group consisting of skin-whiteners, antioxidants, anti-inflammatories, and humectants.

3. The method of claim 2, wherein said further ingredient is derived from a plant extract.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a forward primer
      for PCR reaction of involucrin (INV) gene

<400> SEQUENCE: 1
tgaaacagcc aactccactg                                              20

<210> SEQ ID NO 2
<211> LENGTH: 20
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a reverse primer
      for PCR reaction of involucrin (INV) gene

<400> SEQUENCE: 2
taagctgctg ctctgggttt                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a forward primer
      for PCR reaction of profilaggrin (PFG) gene

<400> SEQUENCE: 3
ggcaaatcct gaagaatcca                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a reverse primer
      for PCR reaction of profilaggrin (PFG) gene

<400> SEQUENCE: 4
tgctttctgt gcttgtgtcc                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a forward primer
      for PCR reaction of beta-glucocerebrosidase (GCase) gene

<400> SEQUENCE: 5
gcagccagaa cagaagttcc                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a reverse primer
      for PCR reaction of beta-glucocerebrosidase (GCase) gene

<400> SEQUENCE: 6 atcagggtg tctgcatagg                                                  20

<210> SEQ ID NO 7
<211> LENGTH: 20
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a forward primer
      for PCR reaction of sphingomyelinase (SMase) gene

<400> SEQUENCE: 7
tgaagagctg gagctggaat                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a reverse primer
      for PCR reaction of sphingomyelinase (SMase) gene

<400> SEQUENCE: 8
gagctcccgg agtagtttcc                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a forward primer
      for PCR reaction of cyclophilin B (CypB) gene

<400> SEQUENCE: 9
acaggagaga aaggatttgg                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a reverse primer
      for PCR reaction of cyclophilin B (CypB) gene

<400> SEQUENCE: 10
ctgtcgtgat gaagaactgg                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a forward primer
      for PCR reaction of keratinocyte growth factor (KGF) gene

<400> SEQUENCE: 11
atgaacaccc ggagcactac                                                   20

<210> SEQ ID NO 12
```

```
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a reverse primer
      for PCR reaction of keratinocyte growth factor (KGF) gene

<400> SEQUENCE: 12
gggctggaac agttcacatt                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a forward primer
      for PCR reaction of 18s RNA gene

<400> SEQUENCE: 13
ggacacggac aggattgaca                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A nucleotide sequence used as a reverse primer
      for PCR reaction of 18s RNA gene

<400> SEQUENCE: 14
acccacggaa tcgagaaaga                                                 20
```